United States Patent
Bartus et al.

(10) Patent No.: US 6,514,482 B1
(45) Date of Patent: Feb. 4, 2003

(54) PULMONARY DELIVERY IN TREATING DISORDERS OF THE CENTRAL NERVOUS SYSTEM

(75) Inventors: Raymond T. Bartus, Sudbury, MA (US); Dwaine F. Emerich, Cranston, RI (US)

(73) Assignee: Advanced Inhalation Research, Inc., Cambridge, MA (US)

( * ) Notice: Subject to any disclaimer, the term of this patent is extended or adjusted under 35 U.S.C. 154(b) by 0 days.

(21) Appl. No.: 09/665,252

(22) Filed: Sep. 19, 2000

(51) Int. Cl.[7] .............. A61K 9/12; A61K 9/14; A61K 9/72
(52) U.S. Cl. .............. 424/45; 424/43; 424/789; 514/220; 128/203.15
(58) Field of Search ................ 514/220, 252, 514/255; 424/45, 489; 128/203.15; 560/43

(56) References Cited

U.S. PATENT DOCUMENTS

| | | | |
|---|---|---|---|
| 4,814,161 A | 3/1989 | Jinks et al. ............. 424/45 |
| 4,895,719 A | 1/1990 | Radhakrishnan et al. ..... 424/45 |
| 5,118,494 A | 6/1992 | Schultz et al. ............ 424/45 |
| 5,166,202 A | 11/1992 | Schweizer ................ 514/220 |
| 5,284,133 A | 2/1994 | Burns et al. .......... 128/200.23 |
| 5,354,885 A | * 10/1994 | Millman et al. ............ 560/43 |
| 5,457,100 A | 10/1995 | Daniel ................... 514/220 |
| 5,510,350 A | * 4/1996 | Oxford et al. ............ 514/252 |
| 5,654,007 A | 8/1997 | Johnson et al. ........... 424/489 |
| 5,756,071 A | 5/1998 | Mattern et al. ............ 424/45 |
| 5,855,913 A | 1/1999 | Hanes et al. ............. 424/489 |
| 5,874,064 A | 2/1999 | Edwards et al. ............ 424/46 |
| 5,875,776 A | 3/1999 | Vaghefi ............... 128/203.15 |
| 5,922,354 A | 7/1999 | Johnson et al. ........... 424/489 |
| 5,981,474 A | 11/1999 | Manning et al. ............ 514/2 |
| 5,985,309 A | 11/1999 | Edwards et al. ........... 424/426 |
| 6,019,968 A | 2/2000 | Platz et al. ............ 424/130.1 |
| 6,048,857 A | 4/2000 | Ellinwood, Jr. et al. ..... 514/221 |
| 6,103,270 A | 8/2000 | Johnson et al. ........... 424/489 |
| 6,136,295 A | 10/2000 | Edwards et al. ............ 424/45 |
| 6,165,463 A | 12/2000 | Platz et al. ............ 424/130.1 |
| 6,193,954 B1 | * 2/2001 | Adjei et al. .............. 424/45 |

FOREIGN PATENT DOCUMENTS

| | | |
|---|---|---|
| CA | 2152684 | 6/1995 |
| EP | 0 496 307 A1 | 7/1992 |
| JP | 61022019 | 1/1986 |
| WO | WO 91/16882 | 11/1991 |
| WO | WO 98/31346 | 7/1998 |
| WO | WO 98/46245 | 10/1998 |
| WO | WO 00/72827 A2 | 12/2000 |
| WO | WO 01/95874 A2 | 12/2001 |

OTHER PUBLICATIONS

Journal of the Neurological Sciences, vol. 150, Issue: 1001, supplement 1, p. S198, Sep. 1997.*

* cited by examiner

Primary Examiner—Jose' G. Dees
Assistant Examiner—M. Haghighatian
(74) Attorney, Agent, or Firm—Hamilton, Brook, Smith & Reynolds, P.C.

(57) ABSTRACT

A method of pulmonary delivery of a medicament, for example a dopamine precursor or a dopamine agonist, which includes administering to the respiratory tract of a patient in need of rescue therapy particles comprising an effective amount of a medicament. The particles are delivered to the pulmonary system and are released into the blood stream and delivered to the medicament's site of action in a time sufficiently short to provide the rescue therapy. In addition to the medicament, the particles can include other materials such as, for example, phospholipids, amino acids, combinations thereof and others. Preferred particles have a tap density of less than about 0.4 g/cm$^3$.

42 Claims, 9 Drawing Sheets

PULMONARY DELIVERY IN TREATING DISORDERS OF THE CENTRAL NERVOUS SYSTEM

BACKGROUND OF THE INVENTION

Parkinson's disease is characterized neuropathologically by degeneration of dopamine neurons in the basal ganglia and neurologically by debilitating tremors, slowness of movement and balance problems. It is estimated that over one million people suffer from Parkinson's disease. Nearly all patients receive the dopamine precursor levodopa or L-Dopa, often in conjunction with the dopa-decarboxylase inhibitor, carbidopa. L-Dopa adequately controls symptoms of Parkinson's disease in the early stages of the disease. However, it tends to become less effective after a period which can vary from several months to several years in the course of the disease.

It is believed that the varying effects of L-Dopa in Parkinson's disease patients is related, at least in part, to the plasma half life of L-Dopa which tends to be very short, in the range of 1 to 3 hours, even when co-administered with carbidopa. In the early stages of the disease, this factor is mitigated by the dopamine storage capacity of the targeted striatal neurons. L-Dopa is taken up and stored by the neurons and is released over time. However, as the disease progresses, dopaminergic neurons degenerate, resulting in decreased dopamine storage capacity. Accordingly, the positive effects of L-Dopa become increasingly related to fluctuations of plasma levels of L-Dopa. In addition, patients tend to develop problems involving gastric emptying and poor intestinal uptake of L-Dopa. Patients exhibit increasingly marked swings in Parkinson's disease symptoms, ranging from a return to classic Parkinson's disease symptoms, when plasma levels fall, to the so-called dyskinesis, when plasma levels temporarily rise too high following L-Dopa administration.

As the disease progresses, conventional L-Dopa therapy involves increasingly frequent, but lower dosing schedules. Many patients, for example, receive L-Dopa every two to three hours. It is found, however, that even frequent doses of L-Dopa are inadequate in controlling Parkinson's disease symptoms. In addition, they inconvenience the patient and often result in non-compliance.

It is also found that even with as many as six to ten L-Dopa doses a day, plasma L-Dopa levels can still fall dangerously low, and the patient can experience very severe Parkinson's disease symptoms. When this happens, additional L-Dopa is administered as intervention therapy to rapidly increase brain dopamine activity. However, orally administered therapy is associated with an onset period of about 30 to 45 minutes during which the patient suffers unnecessarily. In addition, the combined effects of the intervention therapy, with the regularly scheduled dose can lead to overdosing, which can require hospitalization. For example, subcutaneously administered dopamine receptor agonist (apomorphine), often requiring a peripherally acting dopamine antagonist, for example, domperidone, to control dopamine-induced nausea, is inconvenient and invasive.

Other medical indications involving the central nervous system (CSN) require rapid delivery of a medicament such as but not limited to epilepsy, panic attacks and migraines. For example, about 2 million people in the USA suffer from some form of epilepsy, with the majority receiving at least one of several different anti-seizure medications. The incidence of status epilepticus (the more serious form of epilepsy) is approximately 250,000. A significant number of patients also suffer from so-called "cluster seizures", wherein an initial seizure forewarns that a series of additional seizures will occur within a relatively short time frame. By some reports, 75% of all patients continue to experience seizures despite taking medication chronically. Poor compliance with the prescribed medications is believed to be a significant (albeit not sole) contributing factor. The importance of controlling or minimizing the frequency and intensity of seizures lies in the fact that incidence of seizures has been correlated with neuronal deficits and is believed to cause loss of neurons in the brain.

Despite chronic treatment, as many as 75% of all patients continue to exhibit periodic seizures. The uncontrolled seizures occur in many forms. In the case of "cluster seizures," one seizure serves notice that a cascade has begun which will lead to a series of seizures before the total episode passes. In certain patients, prior to the onset of a severe seizure, some subjective feeling or sign is detected by the patient (defined as an aura). In both instances, an opportunity exists for these patients to significantly reduce the liability of the seizure through "self medication". While many patients are instructed to do so, the drugs currently available to permit effective self medication are limited.

Panic attacks purportedly affect about 2.5 million people in this country alone. The disorder is characterized by acute episodes of anxiety, leading to difficult breathing, dizziness, heart palpitations and fear of losing control. The disorder is believed to involve a problem with the sympathetic nervous system (involving an exaggerated arousal response, leading to overstimulation of adrenaline release and/or adrenergic neurons). Benzodiazepines are effective against these attacks.

A pure vasogenic etiology/pathogenesis for migraine was first proposed in the 1930s; by the 1980s, this was replaced by a neurogenic etiology/pathogenesis, which temporarily won favor among migraine investigators. However, it is now generally recognized that both vasogenic and neurogenic components are involved, interacting as a positive feedback system, with each continuously triggering the other. The major neurotransmitters implicated include serotonin (the site of action of the triptans), substance P (traditionally associated with mediating pain), histamine (traditionally associated with inflammation) and dopamine. The major pathology associated with migraine attacks include an inflammation of the dura, an increase in diameter of meningeal vessels and supersensitivity of the trigeminal cranial nerve, including the branches that enervate the meningeal vessels. The triptans are believed to be effective because they affect both the neural and vascular components of the migraine pathogenic cascade. Migraines include Classic and Common Migraines, Cluster Headaches and Tension Headaches.

Initial studies with sumatriptain showed that, when administered intravenously (IV), a 90% efficacy rate was achieved. However, the efficiency rate is only approximately 60% with the oral form (versus 30% for placebo). The nasal form has proven to be highly variable, requiring training and skill on the part of the patient, which some of the patients do not seem to master. The treatment also induces a bad taste in the mouth which many patients find highly objectionable. There currently exists no clear evidence that any of the recent, more selective 5HT1 receptor agonists are any more efficacious than sumatriptan (which stimulates multiple receptor subtypes; e.g., 1B, 1D, and 1F).

In addition to not providing adequate efficacy, current dosing of triptans have at least two other deficiencies: (1)

vasoconstriction of chest and heart muscles, which produces chest tightness and pain in some subjects; this effect also presents an unacceptable risk to hypertensive and other CV patients, for whom the triptans are contraindicated, and (2) the duration of action of current formulations is limited, causing a return of headache in many patients about 4 hours after initial treatment.

Rapid onset of a hypnotic would also be quite desirable and particularly useful in sleep restoration therapy, as middle of night awakening and difficulty in falling asleep again, once awakened, is common in middle aged and aging adults.

Other indications related to the CNS, such as, for example, mania, bipolar disorders, schizophrenia, appetite suppression, motion sickness, nausea and others, as known in the art, also require rapid delivery of a medicament to its site of action.

Therefore, a need exists for a method of the rapid delivery of medicaments which is at least as effective as conventional therapies yet minimizes or eliminates the above-mentioned problems.

SUMMARY OF THE INVENTION

The invention relates to a method of treating a disorder of the central nervous system. The method includes administering to the respiratory tract of a patient in need of rapid onset or rescue therapy particles comprising an effective amount of a medicament. The particles are delivered to the pulmonary system and the medicament is released into the patient's blood stream and reaches the medicament's site of action in a time interval which is sufficiently short to provide the rescue therapy.

In a preferred embodiment, the disorder of the nervous system is Parkinson's disease. Other disorders of the nervous system, such as, for example, epileptic and other seizures, panic attacks, sleep disorders, migraine and others can be treated by the method of the invention. In a preferred embodiment the medicament employed in the methods of the invention is a dopamine precursor or a dopamine agonist, for example levodopa.

In one embodiment, particles employed in the method of the invention are particles suitable for delivering a medicament to the pulmonary system and in particular to the alveoli or the deep lung. In a preferred embodiment, the particles have a tap density which is less than 0.4 g/cm$^3$. In another preferred embodiment, the particles have a geometric diameter, of at least 5 μm (microns), preferably between about 5 μm and 30 μm. In yet another preferred embodiment, the particles have an aerodynamic diameter between about 1 μm and about 5 μm.

Particles can consist of the medicament or can further include one or more additional components. Rapid release of the medicament into the blood stream and its delivery to its site of action, for example, the central nervous system, is preferred. In one embodiment of the invention, the particles include a material which enhances the release kinetics of the medicament. Examples of suitable such materials include, but are not limited to, certain phospholipids, amino acids, carboxylate moieties combined with salts of multivalent metals and others.

Preferably, administration to the respiratory tract is by a dry powder inhaler or by a metered dose inhaler. The particles of the invention also can be employed in compositions suitable for delivery to the pulmonary system such as known in the art.

The invention has many advantages. For example, pulmonary delivery provides on-demand treatment without the inconvenience of injections. Selective delivery of a medicament to the central nervous can be obtained in a time frame not available with oral formulations. Thus, an effective dose can be delivered to the site of action on the "first pass" of the medicament in the circulatory system. By practicing the invention, relief is available to symptomatic patients in a time frame during which conventional oral therapies would still be traveling to the site of action.

DETAILED DESCRIPTION OF THE INVENTION

Figure 1A:
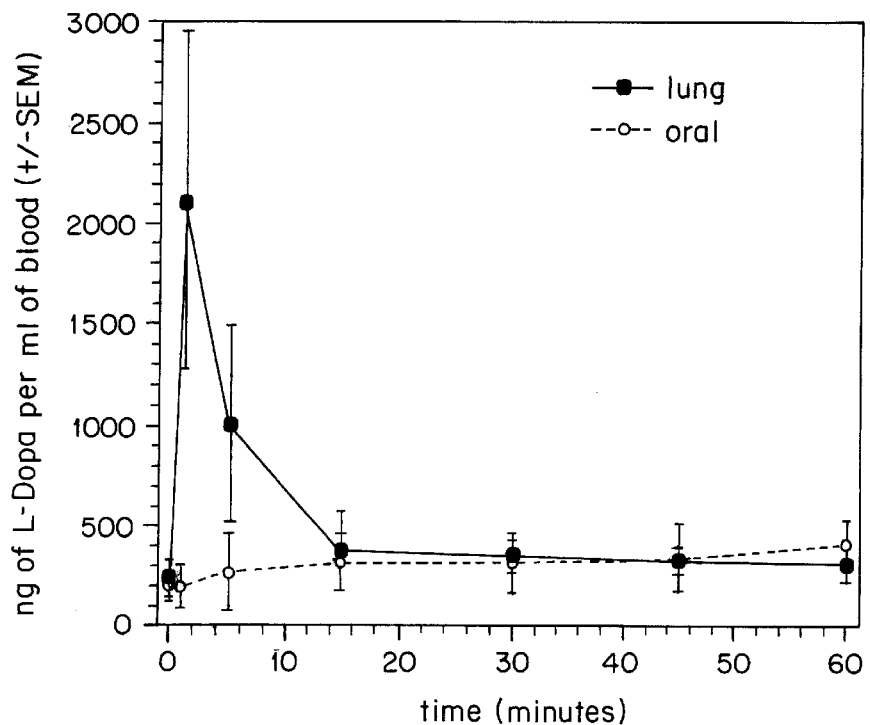
FIG. 1A is a plot representation of blood levels of L-Dopa in rats following administration via oral gavage or direct administration to the lungs measured by mass spectrometer.
Figure 1B:
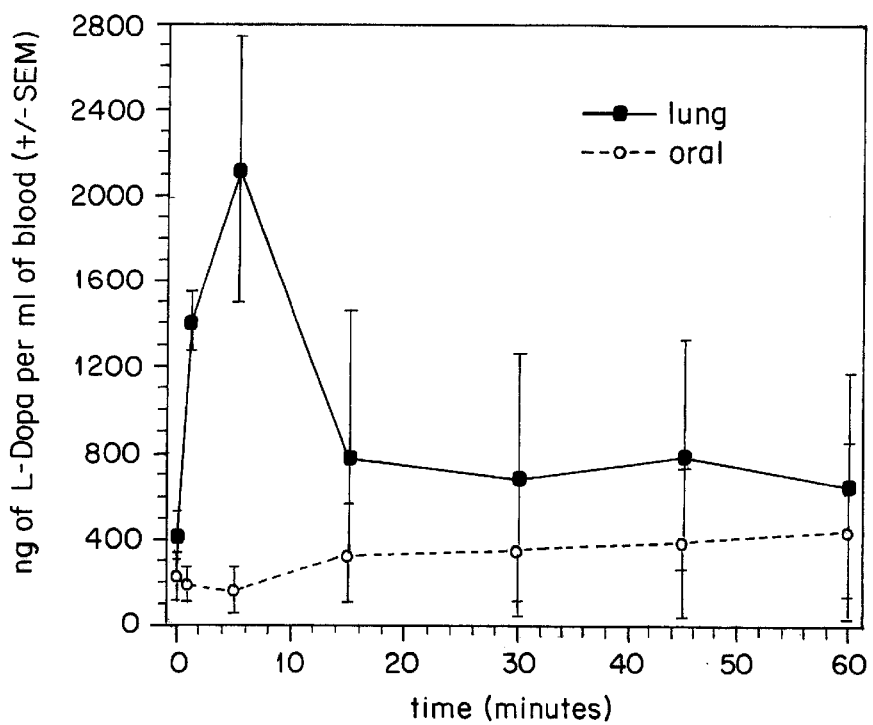
FIG. 1B is a plot representation of blood levels of L-Dopa in rats following administration via oral gavage or direct administration to the lungs measured by HPLC.

The features and other details of the invention, either as steps of the invention or as combination of parts of the invention, will now be more particularly described and pointed out in the claims. It will be understood that the particular embodiments of the invention are shown by way of illustration and not as limitations of the invention. The principle feature of this invention may be employed in various embodiments without departing from the scope of the invention.

The invention is generally related to a method of providing rescue therapy to patients suffering from a disorder of the central nervous system. As used herein, "rescue therapy" means on demand, rapid delivery of a drug to a patient to help reduce or control disease symptoms.

One preferred medical indication which can be treated by the method of the invention is Parkinson's disease, in particular the late stages of the disease.

In addition, forms of epileptical seizures such as occurring in Myoclonic Epilepsies, including Progressive and Juvenile; Partial Epilepsies, including Complex Partial, Frontal Lobe, Motor and Sensory, Rolandic and Temporal Lobe; Benign Neonatal Epilepsy; Post-Traumatic Epilepsy; Reflex Epilepsy; Landau-Kleffner Syndrome; and Seizures, including Febrile, Status Epilepticus, and Epilepsia Partialis Continua also can be treated using the method of the invention.

Sleep disorders that can benefit from the present invention include Dyssomnias, Sleep Deprivation, Circadian Rhythm Sleep Disorders, Intrinsic Sleep Disorders, including Disorders of Excessive Somnolence, Idiopathic Hypersomnolence, Kleine-Levin Syndrome, Narcolepsy, Nocturnal Myoclonus Syndrome, Restless Legs Syndrome, Sleep Apnea Syndromes, Sleep Initiation and Maintenance Disorders, Parasomnias, Nocturnal Nyoclonus Syndrome, Nocturnal Paroxysmal Dystonia, REM Sleep Parasomnias, Sleep Arousal Disorders, Sleep Bruxism, and Sleep-Wake Transition Disorders. Sleep interruption often occurs around 2 to 3 a.m. and requires treatment the effect of which lasts approximately 3 to 4 hours.

Examples of other disorders of the central nervous system which can be treated by the method of the invention include but are not limited to appetite suppression, motion sickness, panic or anxiety attack disorders, nausea suppressions, mania, bipolar disorders, schizophrenia and others, known in the art to require rescue therapy.

Medicaments which can be used in the method of the invention include pharmaceutical preparations such as those generally prescribed in the rescue therapy of disorders of the nervous system. In a preferred embodiment, the medicament is a dopamine precursor, dopamine agonist or any combination thereof. Preferred dopamine precursors include levodopa (L-Dopa). Other drugs generally administered in the treatment of Parkinson's disease and which may be suitable in the methods of the invention include, for example, ethosuximide, dopamine agonists such as, but not limited to carbidopa, apomorphine, sopinirole, pramipexole, pergoline, bronaocriptine. The L-Dopa or other dopamine precursor or agonist may be any form or derivative that is biologically active in the patient being treated.

Examples of anticonvulsants include but are not limited to diazepam, valproic acid, divalproate sodium, phenytoin, phenytoin sodium, cloanazepam, primidone, phenobarbital, phenobarbital sodium, carbamazepine, amobarbital sodium, methsuximide, metharbital, mephobarbital, mephenytoin, phensuximide, pararnethadione, ethotoin, phenacemide, secobarbitol sodium, clorazepate dipotassium, trimethadione. Other anticonvulsant drugs include, for example, Acetazolamide, Carbamazepine, Chlormethiazole, Clonazepam, Clorazepate Dipotassium, Diazepam, Dimethadione, Estazolam, Ethosuximide, Flunarizine, Lorazepam, Magnesium Sulfate, Medazepam, Melatonin, Mephenytoin, Mephobarbital, Meprobamate, Nitrazepam, Paraldehyde, Phenobarbital, Phenytoin, Primidone, Propofol, Riluzole, Thiopental, Tiletamine, Trimethadione, Valproic Acid, Vigabatrin. A preferred drug is the benzodiazepines, for instance, Alprazolam, Chlordiazepoxide, Clorazepate Dipotassium, Estazolam, Medazepam, Midazolam, Triazolam, as well as Benzodiazepinones, including Anthramycin, Bromazepam, Clonazepam, Devazepide, Diazepam, Flumazenil, Flunitrazepam, Flurazepam, Lorazepam, Nitrazepam, Oxazepam, Pirensepine, Prazepam, and Temazepam.

Examples of drugs for providing symptomatic relief for migraines include the non-steroidal anti-inflammatory drugs (NSAIDs). Generally, parenteral NSAIDs are more effective against migraine than oral forms. Among the various NSIADs, ketoprofen is considered by many to be one of the more effective for migraine. Its $T_{max}$ via the oral route, however, is about 90 min. Other NSAIDs include Aminopyrine, Amodiaquine, Ampyrone, Antipyrine, Apazone, Aspirin, Benzydamine, Bromelains, Bufexamac, BW-755C, Clofazimine, Clonixin, Curcumin, Dapsone, Diclofenac, Diflunisal, Dipyrone, Epirizole, Etodolac, Fenoprofen, Flufenamic Acid, Flurbiprofen, Glycyrrhizic Acid, Ibuprofen, Indomethacin, Ketorolac, Ketorolac Tromethamine, Meclofenamic Acid, Mefenamic Acid, Mesalamine, Naproxen, Niflumic Acid, Oxyphenbutazone, Pentosan Sulfuric Polyester, Phynylbutazone, Piroxicam, Prenazone, Salicylates, Sodium Salicylate, Sulfasalazine, Sulindac, Suprofen, and Tolmetin.

Other antimigraine agents include triptans, ergotamine tartrate, propanolol hydrochloride, isometheptene mucate, dichloralphenazone, and others.

Preferred drugs for sleep disorders include the benzodiazepines, for instance, Alprazolam, Chlordiazepoxide, Clorazepate Dipotassium, Estazolam, Medazepam, Midazolam, Triazolam, as well as Benzodiazepinones, including Anthramycin, Bromazepam, Clonazepam, Devazepide, Diazepam, Flumazenil, Flunitrazepam, Flurazepam, Lorasepam, Nitrazepam, Oxazepam, Pirenzepine, Prazepam, Temazepam, and Triazolam. Another drug is Zolpidem (Ambien) which is currently given as a 5 mg tablet with $T_{max}$=1.6 hours; ½ Life=2.6 hours (range between 1.4 to 4.5 hours). Peak plasma levels are reached in about 2 hours with a half-life of about 1.5 to 5.5 hours. Still another drug is Halcion (Ambien) which is a heterocyclic benzodiazepine derivative with a molecular weight of 343 which is soluble in alcohol but poorly soluble in water. The usual dose by mouth is 0.125 and 0.25 mg. Temazepam may be a good candidate for sleep disorders due to a longer duration of action that is sufficient to maintain sleep throughout the night. Zaleplam (Sonata, Wyeth) is one drug currently approved for middle of night sleep restoration due to its short duration of action.

Other medicaments include analgesics/antipyretics for example, ketoprofin, flurbiprofen, aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate, and others.

Antianxiety medications include, for example, lorazepam, buspirone hydrochloride, prazepam, chlordizepoxide hydrochloride, oxazepam, clorazepate dipotassium, diazepam, hydroxyzine pamoate, hydroxyzine hydrochloride, alprazolam, droperidol, halazepam, chlormezanone, and others.

Examples of antipsychotic agents include haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like.

One example of an antimonic agent is lithium carbonate while examples of Alzheimer agents include tetra amino acridine, donapezel, and others.

Sedatives/hypnotics include barbiturates (e.g., pentobarbital, phenobarbital sodium, secobarbital sodium), benzodiazepines (e.g., flurazepam hydrochloride, triazolam, tomazeparm, midazolam hydrochloride), and others;

Hypoglycemic agents include, for example, ondansetron, granisetron, meclizine hydrochloride, nabilone, prochlorperazine, dimenhydrinate, promethazine hydrochloride, thiethylperazine, scopolamine, and others. Antimotion sickness agents include, for example, cinnorizine.

Combination of drugs and combination of excipients can be prepared and administered.

Particles including a medicament, for example, one or more of the drugs listed above, are administered to the respiratory tract of a patient in need of rescue therapy. Administration of particles to the respiratory system can be by means such as known in the art. For example, particles are delivered from an inhalation device. In a preferred embodiment, particles are administered via a dry powder inhaler (DPI). Metered-dose-inhalers (MDI), nebulizers or instillation techniques also can be employed.

Methods of administering particles to patients in acute distress are disclosed. These particles of the instant invention are capable of being delivered to the lung and absorbed into the system when other conventional means of delivering drugs fail. In one embodiment, delivery to the pulmonary system of particles in a single, breath-actuated step is enhanced by employing particles which are dispersed at relatively low energies, such as, for example, at energies typically supplied by a subject's inhalation. Such energies are referred to herein as "low." As used herein, "low energy administration" refers to administration wherein the energy applied to disperse and/or inhale the particles is in the range typically supplied by a subject during inhaling.

In particular, properties of the particles enable delivery to patients with highly comprised lungs where other particles prove ineffective for those lacking the capacity to strongly inhale, such as young patients, old patients, infirm patients, or patients with asthma or other breathing difficulties. Further, patients suffering from a combination of ailments may simply lack the ability to sufficiently inhale. Thus, using the methods and particles for the invention, even a weak inhalation is sufficient to deliver the desired dose. This is particularly important when using the particles of the instant invention as rescue therapy for a patient suffering from debilitating illness of the central nervous system for example but not limited to migraine, anxiety, psychosis, depression, bipolar disorder, obsessive compulsive disorder (OCD), convulsions, seizures, epilepsy, Alzheimer's, and especially, Parkinson's disease.

Various suitable devices and methods of inhalation which can be used to administer particles to a patient's respiratory tract are known in the art. For example, suitable inhalers are described in U.S. Pat. No. 4,069,819, issued Aug. 5, 1976 to Valentini, et al., U.S. Pat. No. 4,995,385 issued Feb. 26, 1991 to Valentini, et al., and U.S. Pat. No. 5,997,848 issued Dec. 7, 1999 to Patton, et al. Other examples include, but are not limited to, the Spinhaler® (Fisons, Loughborough, U.K.), Rotahaler® (Glaxo-Wellcome, Research Triangle Technology Park, N.C.), FlowCaps® (Hovione, Loures, Portugal), Inhalator® (Boehringer-Ingelheim, Germany), and the Aerolizer® (Novartis, Switzerland), the diskhaler (Glaxo-Wellcome, RTP, NC) and others, such as known to those skilled in the art.

Preferably, particles administered to the respiratory tract travel through the upper airways (oropharynx and larynx), the lower airways which include the trachea followed by bifurcations into the bronchi and bronchioli and through the terminal bronchioli which in turn divide into respiratory bronchioli leading then to the ultimate respiratory zone, the alveoli or the deep lung. In a preferred embodiment of the invention, most of the mass of particles deposits in the deep lung. In another embodiments of the invention, delivery is primarily to the central airways. Delivery to the upper airways can also be obtained.

In one embodiment of the invention, delivery to the pulmonary system of particles is in a single, breath-actuated step, as describe in U.S. Patent Application, High Efficient Delivery of a Large Therapeutic Mass Aerosol, application Ser. No. 09/591,307, filed Jun. 9, 2000, which is incorporated herein by reference in its entirety. In another embodiment of the invention, at least 50% of the mass of the particles stored in the inhaler receptacle is delivered to a subject's respiratory system in a single, breath-activated step. In a further embodiment, at least 5 milligrams and preferably at least 10 milligrams of a medicament is delivered by administering, in a single breath, to a subject's respiratory tract particles enclosed in the receptacle. Amounts as high as 15, 20, 25, 30, 35, 40 and 50 milligrams can be delivered.

In one embodiment of the invention the particles consist of a medicament, such as, for example, one of the medicaments described above. In another embodiment, the particles include one or more additional components. The amount of drug or medicament present in the particles can range 1.0 to about 90.0 weight percent.

Preferably, the particles include one or more component (s) which promote(s) the fast release of the medicament into the blood stream. As used herein, rapid release of the medicament into the blood stream refers to release kinetics that are suitable for providing rescue therapy. In a preferred embodiment, optimal therapeutic concentration is achieved in less than 10 minutes.

In a preferred embodiment, the particles include one or more phospholipids, such as, for example, a phosphatidylcholine, phosphatidylethanolamine, phosphatidylglycerol, phosphatidylserine, phosphatidylinositol or a conbination thereof. In one embodiment, the phospholipids are endogenous to the lung. Specific examples of phospholipids are shown below.

| | |
|---|---|
| Dilaurylolyphosphatidylcholine (C12;0) | DLPC |
| Dimyristoylphosphatidylcholine (C14;0) | DMPC |
| Dipalmitoylphosphatidylcholine (C16:0) | DPPC |
| Distearoylphosphatidylcholine (18:0) | DSPC |
| Dioleoylphosphatidylcholine (C18:1) | DOPC |
| Dilaurylolyphosphatidylglycerol | DLPG |
| Dimyristoylphosphatidylglycerol | DMPG |
| Dipalmitoylphosphatidylglycerol | DPPG |
| Distearoylphosphatidylglycerol | DSPG |
| Dioleoylphosphatidylglycerol | DOPG |

| -continued | |
|---|---|
| Dimyristoyl phosphatidic acid | DMPA |
| Dipalmitoyl phosphatidic acid | DPPA |
| Dimyristoyl phosphatidylethanolamine | DMPE |
| Dipalmitoyl phosphatidylethanolamine | DPPE |
| Dimyristoyl phosphatidylserine | DMPS |
| Dipalmitoyl phosphatidylserine | DPPS |
| Dipalmitoyl sphingomyelin | DPSP |
| Distearoyl sphingomyelin | DSSP |

Combinations of phospholipids can also be employed.

The phospholipid can be present in the particles in an amount ranging from about 0 to about 90 weight %. Preferably, it can be present in the particles in an amount ranging from about 10 to about 60 weight %.

The phospholipids or combinations thereof can be selected to impart control release properties to the particles. Particles having controlled release properties and methods of modulating release of a biologically active agent are described in U.S. Provisional Patent Application No. 60/150,742 entitled Modulation of Release From Dry Powder Formulations by Controlling Matrix Transition, filed on Aug. 25, 1999 and U.S. Non-Provisional Patent Application, filed on Aug. 23, 2000, with the title Modulation of Release From Dry Powder Formulations under Ser. No. 09/644,736. The contents of both are incorporated herein by reference in their entirety. Rapid release, preferred in the delivery of a rescue therapy medicament, can be obtained for example, by including in the particles phospholipids characterized by low transition temperatures. In another embodiment, a combination of rapid with controlled release particles would allow a rescue therapy coupled with a more sustained release in a single cause of therapy.

In another embodiment of the invention the particles can include a surfactant. As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to microparticles, they tend to present moieties to the external environment that do not attract similarly-coated particles, thus reducing particle agglomeration. Surfactants may also promote absorption of a therapeutic or diagnostic agent and increase bioavailability of the agent.

In addition to lung surfactants, such as, for example, phospholipids discussed above, suitable surfactants include but are not limited to hexadecanol; fatty alcohols such as polyethylene glycol (PEG); polyoxyethylene-9-lauryl ether; a surface active fatty acid, such as palmitic acid or oleic acid; glycocholate; surfactin; a poloxomer; a sorbitan fatty acid ester such as sorbitan trioleate (Span 85); and tyloxapol.

The surfactant can be present in the particles in an amount ranging from about 0 to about 90 weight %. Preferably, it can be present in the particles in an amount ranging from about 10 to about 60 weight %.

Methods of preparing and administering particles including surfactants, and, in particular phospholipids, are disclosed in U.S. Pat. No 5,855,913, issued on Jan. 5, 1999 to Hanes et al. and in U.S. Pat. No. 5,985,309, issued on Nov. 16, 1999 to Edwards et al. The teachings of both are incorporated herein by reference in their entirety.

In another embodiment of the invention, the particles include an amino acid. Hydrophobic amino acids are preferred. Suitable amino acids include naturally occurring and non-naturally occurring hydrophobic amino acids.

Examples of amino acids which can be employed include, but are not limited to: glycine, proline, alanine, cysteine, methionine, valine, leucine, tyrosine, isoleucine, phenylalanine, tryptophan. Preferred hydrophobic amino acids, include but not limited to, leucine, isoleucine, alanine, valine, phenylalanine, glycine and tryptophan. Amino acids include combinations of hydrophobic amino acids can also be employed. Non-naturally occurring amino acids include, for example, beta-amino acids. Both D, L and racemic configurations of hydrophobic amino acids can be employed. Suitable hydrophobic amino acids can also include amino acid analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic C1–C8 hydrocarbons which are completely saturated, which contain one or two heteroatoms such as nitrogen, oxygen or sulfur and/or which contain one or more units of unsaturation. Aromatic groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridintyl.

Suitable substituents on an aliphatic, aromatic or benzyl group include —OH, halogen (—Br, —Cl, —I and —F) —O(aliphatic, substituted aliphatic, benzyl, substituted benzyl, aryl or substituted aryl group), —CN, —NO$_2$, —COOH, —NH$_2$, —NH(aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO (aliphatic group, substituted aliphatic, benzyl, substituted benzyl, aryl or substituted aryl group), —CONH$_2$, —CONH (aliphatic, substituted aliphatic group, benzyl, substituted benzyl, aryl or substituted aryl group)), —SH, —S(aliphatic, substituted aliphatic, benzyl, substituted benzyl, aromatic or substituted aromatic group) and —NH—C(=NH)—NH$_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents. Modifying an amino acid substituent can increase, for example, the lypophilicity or hydrophobicity of natural amino acids which are hydrophillic.

A number of the suitable amino acids, amino acids analogs and salts thereof can be obtained commercially. Others can be synthesized by methods known in the art. Synthetic techniques are described, for example, in Green and Wuts, "*Protecting Groups in Organic Synthesis*", John Wiley and Sons, Chapters 5 and 7, 1991.

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term hydrophobic amino acid refers to an amino acid that, on the hydrophobicity scale has a value greater or equal to 0.5, in other words, has a tendency to partition in the nonpolar acid which is at least equal to that of glycine.

Combinations of hydrophobic amino acids can also be employed. Furthermore, combinations of hydrophobic and hydrophilic (preferentially partitioning in water) amino acids, where the overall combination is hydrophobic, can also be employed. Combinations of one or more amino acids and one or more phospholipids or surfactants can also be employed. Materials which impart fast release kinetics to the medicament are preferred.

The amino acid can be present in the particles of the invention in an amount of at least 10 weight %. Preferably, the amino acid can be present in the particles in an amount ranging from about 20 to about 80 weight %. The salt of a hydrophobic amino acid can be present in the particles of the invention in an amount of at least 10% weight. Preferably, the amino acid salt is present in the particles in an amount ranging from about 20 to about 80 weight %. Methods of forming and delivering particles which include an amino acid are described in U.S. patent application Ser. No. 09/382, 959, filed on Aug. 25, 1999, entitled Use of Simple Amino Acids to Form Porous Particles During Spray Drying, the teachings of which are incorporated herein by reference in their entirety and in U.S. Non-Provisional Patent Application filed on Aug. 23, 2000, titled Use of Simple Amino Acids to Form Porous Particles, under Ser. No. 09/644,320; the teachings of both are incorporated herein by reference in their entirety.

In another embodiment of the invention, the particles include a carboxylate moiety, such as a hydroxydicarboxylic acid or salt thereof, a hydroxytricarboxylic acid or salt thereof, and a multivalent metal salt. One or more phospholipids also can be included. Such compositions are described in U.S. Provisional Application No. 60/150,662, filed on Aug. 25, 1999, entitled Formulation for Spray-Drying Large Porous Particles, and U.S. Non-Provisional Patent Application filed on Aug. 23, 2000, titled Formulation for Spray-Drying Large Porous Particles, under Ser. No. 09/644,105; the teachings of both are incorporated herein by reference in their entirety. In a preferred embodiment, the particles include sodium citrate and calcium chloride.

Other materials, preferably materials which promote fast release kinetics of the medicament can also be employed. For example, biocompatible, and preferably biodegradable polymers can be employed. Particles including such polymeric materials are described in U.S. Pat. No. 5,874,064, issued on Feb. 23, 1999 to Edwards et al., the teachings of which are incorporated herein by reference in their entirety.

The particles can also include a material such as, for example, dextran, polysaccharides, lactose, trehalose, cyclodextrins, proteins, peptides, polypeptides, fatty acids, inorganic compounds, phosphates.

In a preferred embodiment, the particles of the invention have a tap density less than about 0.4 g/cm³. Particles which have a tap density of less than about 0.4 g/cm³ are referred herein as "aerodynamically light particles". More preferred are particles having a tap density less than about 0.1 g/cm³. Tap density can be measured by using instruments known to those skilled in the art such as but not limited to the Dual Platform Microprocessor Controlled Tap Density Tester (Vankel, N.C.) or a GeoPyC™ instrument (Micrometrics Instrument Corp., Norcross, Ga. 30093). Tap density is a standard measure of the envelope mass density. Tap density can be determined using the method of USP Bulk Density and Tapped Density, United States Pharmacopeia convention, Rockville, Md., 10$^{th}$ Supplement, 4950–4951, 1999. Features which can contribute to low tap density include irregular surface texture and porous structure.

The envelope mass density of an isotropic particle is defined as the mass of the particle divided by the minimum sphere envelope volume within which it can be enclosed. In one embodiment of the invention, the particles have an envelope mass density of less than about 0.4 g/cm³.

Aerodynamically light particles have a preferred size, e.g., a volume median geometric diameter (VMGD) of at least about 5 microns ($\mu$m). In one embodiment, the VMGD is from about 5 $\mu$m to about 30 $\mu$m. In another embodiment of the invention, 1 5 the particles have a VMGD ranging from about 10 $\mu$m to about 30 $\mu$m. In other embodiments, the particles have a median diameter, mass median diameter (MMD), a mass median envelope diameter (MMED) or a mass median geometric diameter (MMGD) of at least 5 $\mu$m, for example from about 5 $\mu$m and about 30 $\mu$m.

The diameter of the spray-dried particles, for example, the VMGD, can be measured using an electrical zone sensing instrument such as a Multisizer IIe, (Coulter Electronic, Luton, Beds, England), or a laser diffraction instrument (for example Helos, manufactured by Sympatec, Princeton, N.J.). Other instruments for measuring particle diameter are well know in the art. The diameter of particles in a sample will range depending upon factors such as particle composition and methods of synthesis. The distribution of size of particles in a sample can be selected to permit optimal deposition to targeted sites within the respiratory tract.

Aerodynamically light particles preferably have "mass median aerodynamic diameter" (MMAD), also referred to herein as "aerodynamic diameter", between about 1 $\mu$m and about 5 $\mu$m. In another embodiment of the invention, the MMAD is between about 1 $\mu$m and about 3 $\mu$m. In a further embodiment, the MMAD is between about 3 $\mu$m and about 5 $\mu$m.

Experimentally, aerodynamic diameter can be determined by employing a gravitational settling method, whereby the time for an ensemble of particles to settle a certain distance is used to infer directly the aerodynamic diameter of the particles. An indirect method for measuring the mass median aerodynamic diameter (MMAD) is the multi-stage liquid impinger (MSLI).

The aerodynamic diameter, $d_{aer}$, can be calculated from the equation:

$$d_{aer} = d_g \sqrt{\rho_{tap}}$$

where $d_g$ is the geometric diameter, for example the MMGD and $\rho$ is the powder density.

Particles which have a tap density less than about 0.4 g/cm³, median diameters of at least about 5 $\mu$m, and an aerodynamic diameter of between about 1 $\mu$m and about 5 $\mu$m, preferably between about 1 $\mu$m and about 3 $\mu$m, are more capable of escaping inertial and gravitational deposition in the oropharyngeal region, and are targeted to the airways, particularly the deep lung. The use of larger, more porous particles is advantageous since they are able to aerosolize more efficiently than smaller, denser aerosol particles such as those currently used for inhalation therapies.

In comparison to smaller, relatively denser particles the larger aerodynamically light particles, preferably having a median diameter of at least about 5 $\mu$m, also can potentially more successfully avoid phagocytic engulfment by alveolar macrophages and clearance from the lungs, due to size exclusion of the particles from the phagocytes' cytosolic space. Phagocytosis of particles by alveolar macrophages diminishes precipitously as particle diameter increases beyond about 3 μm. Kawaguchi, H., et al., *Biomaterials* 7: 61–66 (1986); Krenis, L. J. and Strauss, B., *Proc. Soc. Exp. Med.*, 107: 748–750 (1961); and Rudt, S. and Muller, R. H., *J. Contr. Rel.*, 22: 263–272 (1992). For particles of statistically isotropic shape, such as spheres with rough surfaces, the particle envelope volume is approximately equivalent to the volume of cytosolic space required within a macrophage for complete particle phagocytosis.

The particles may be fabricated with the appropriate material, surface roughness, diameter and tap density for localized delivery to selected regions of the respiratory tract such as the deep lung or upper or central airways. For example, higher density or larger particles may be used for upper airway delivery, or a mixture of varying sized particles in a sample, provided with the same or different therapeutic agent may be administered to target different regions of the lung in one administration. Particles having an aerodynamic diameter ranging from about 3 to about 5 μm are preferred for delivery to the central and upper airways. Particles having and aerodynamic diameter ranging from about 1 to about 3 μm are preferred for delivery to the deep lung.

Inertial impaction and gravitational settling of aerosols are predominant deposition mechanisms in the airways and acini of the lungs during normal breathing conditions. Edwards, D. A., *J. Aerosol Sci.*, 26: 293–317 (1995). The importance of both deposition mechanisms increases in proportion to the mass of aerosols and not to particle (or envelope) volume. Since the site of aerosol deposition in the lungs is determined by the mass of the aerosol (at least for particles of mean aerodynamic diameter greater than approximately 1 μm), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, daer, is related to the envelope sphere diameter, d (Gonda, I., "Physico-chemical principles in aerosol delivery," in *Topics in Pharmaceutical Sciences* 1991 (eds. D. J. A. Crommelin and K. K. Midha), pp. 95–117, Stuttgart: Medpharm Scientific Publishers, 1992)), by the formula:

$$d_{aer}=d\sqrt{\rho}$$

where the envelope mass ρ is in units of g/cm³. Maximal deposition of monodispersed aerosol particles in the alveolar region of the human lung (~60%) occurs for an aerodynamic diameter of approximately $d_{aer}=3$ μm. Heyder, J. et al., *J. Aerosol Sci.*, 17: 811–825 (1986). Due to their small envelope mass density, the actual diameter d of aerodynamically light particles comprising a monodisperse inhaled powder that will exhibit maximum deep-lung deposition is:

$$d=3/\sqrt{\rho}\mu m \text{ (where } \rho<1 \text{ g/cm}^3\text{)};$$

where d is always greater than 3 μm. For example, aerodynamically light particles that display an envelope mass density, ρ=0.1 g/cm³, will exhibit a maximum deposition for particles having envelope diameters as large as 9.5 μm. The increased particle size diminishes interparticle adhesion forces. Visser, J., *Powder Technology*, 58: 1–10. Thus, large particle size increases efficiency of aerosolization to the deep lung for particles of low envelope mass density, in addition to contributing to lower phagocytic losses.

The aerodynamic diameter can be calculated to provide for maximum deposition within the lungs. Previously this was achieved by the use of very small particles of less than about five microns in diameter, preferably between about one and about three microns, which are then subject to phagocytosis. Selection of particles which have a larger diameter, but which are sufficiently light (hence the characterization "aerodynamically light"), results in an equivalent delivery to the lungs, but the larger size particles are not phagocytosed. Improved delivery can be obtained by using particles with a rough or uneven surface relative to those with a smooth surface.

In another embodiment of the invention, the particles have an envelope mass density, also referred to herein as "mass density" of less than about 0.4 g/cm³. Particles also having a mean diameter of between about 5 μm and about 30 μm are preferred. Mass density and the relationship between mass density, mean diameter and aerodynamic diameter are discussed in U.S. application Ser. No. 08/655,570, filed on May 24, 1996, which is incorporated herein by reference in its entirety. In a preferred embodiment, the aerodynamic diameter of particles having a mass density less than about 0.4 g/cm³ and a mean diameter of between about 5 μm and about 30 μm mass mean aerodynamic diameter is between about 1 μm and about 5 μm.

Suitable particles can be fabricated or separated, for example by filtration or centrifugation, to provide a particle sample with a preselected size distribution. For example, greater than about 30%, 50%, 70%, or 80% of the particles in a sample can have a diameter within a selected range of at least about 5 μm. The selected range within which a certain percentage of the particles must fall may be for example, between about 5 and about 30 μm, or optimally between about 5 and about 15 μm. In one preferred embodiment, at least a portion of the particles have a diameter between about 9 and about 11 μm. Optionally, the particle sample also can be fabricated wherein at least about 90%, or optionally about 95% or about 99%, have a diameter within the selected range. The presence of the higher proportion of the aerodynamically light, larger diameter particles in the particle sample enhances the delivery of therapeutic or diagnostic agents incorporated therein to the deep lung. Large diameter particles generally mean particles having a median geometric diameter of at least about 5 μm.

In a preferred embodiment, suitable particles which can be employed in the method of the invention are fabricated by spray drying. In one embodiment, the method includes forming a mixture including L-Dopa or another medicament, or a combination thereof, and a surfactant, such as, for example, the surfactants described above. In a preferred embodiment, the mixture includes a phospholipid, such as, for example the phospholipids described above. The mixture employed in spray drying can include an organic or aqueous-organic solvent.

Suitable organic solvents that can be employed include but are not limited to alcohols for example, ethanol, methanol, propanol, isopropanol, butanols, and others. Other organic solvents include but are not limited to per fluorocarbons, dichloromethane, chloroform, ether, ethyl acetate, methyl tert-butyl ether and others.

Co-solvents include an aqueous solvent and an organic solvent, such as, but not limited to, the organic solvents as described above. Aqueous solvents include water and buffered solutions. In one embodiment, an ethanol water solvent is preferred with the ethanol:water ratio ranging from about 50:50 to about 90:10 ethanol:water.

The spray drying mixture can have a neutral, acidic or alkaline pH. Optionally, a pH buffer can be added to the solvent or co-solvent or to the formed mixture. Preferably, the pH can range from about 3 to about 10.

Suitable spray-drying techniques are described, for example, by K. Masters in "Spray Drying Handbook", John Wiley & Sons, New York, 1984. Generally, during spray-drying, heat from a hot gas such as heated air or nitrogen is used to evaporate the solvent from droplets formed by atomizing a continuous liquid feed. Other spray-drying techniques are well known to those skilled in the art. In a preferred embodiment, a rotary atomizer is employed. An examples of suitable spray driers using rotary atomization includes the Mobile Minor spray drier, manufactured by Niro, Denmark. The hot gas can be, for example, air, nitrogen or argon.

Figure 2A:
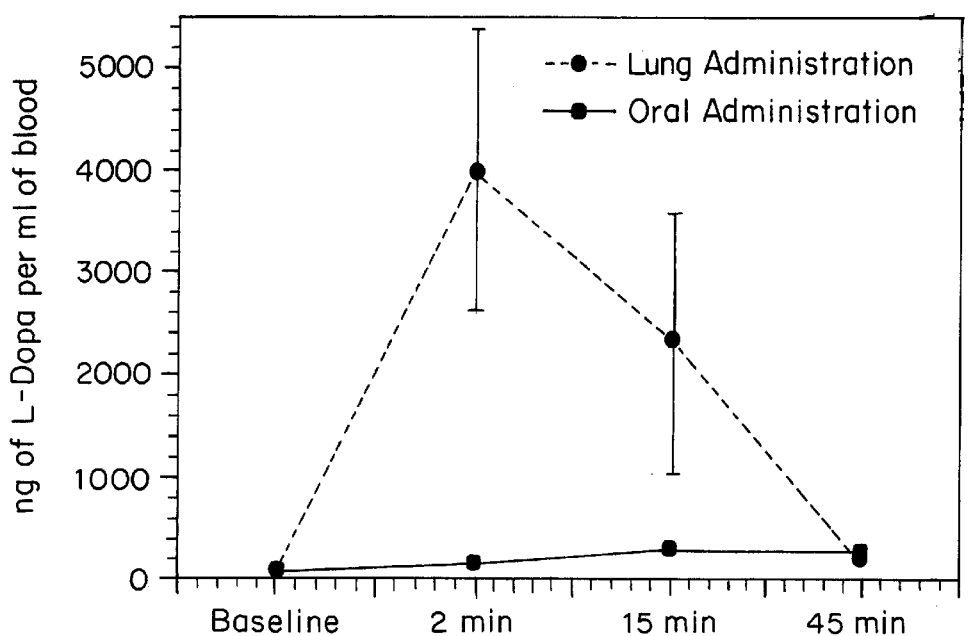
FIG. 2A is a plot representation of blood L-Dopa levels in rats.

The particles can be fabricated with a rough surface texture to reduce particle agglomeration and improve flowability of the powder. The spray-dried particles have improved aerosolization properties. The spray-dried particle can be fabricated with features which enhance aerosolization via dry powder inhaler devices, and lead to lower deposition in the mouth, throat and inhaler device.

The particles of the invention can be employed in compositions suitable for drug delivery to the pulmonary system. For example, such compositions can include the particles and a pharmaceutically acceptable carrier for administration to a patient, preferably for administration via inhalation. The particles may be administered alone or in any appropriate pharmaceutically acceptable carrier, such as a liquid, for example saline, or a powder, for administration to the respiratory system. They can be co-delivered with larger carrier particles, not including a therapeutic agent, the latter possessing mass median diameters for example in the range between about 50 $\mu$m and about 100 $\mu$m.

Aerosol dosage, formulations and delivery systems may be selected for a particular therapeutic application, as described, for example, in Gonda, I. "Aerosols for delivery of therapeutic and diagnostic agents to the respiratory tract," in *Critical Reviews in Therapeutic Drug Carrier Systems,* 6: 273–313, 1990; and in Moren, "Aerosol dosage forms and formulations," in: *Aerosols in Medicine. Principles, Diagnosis and Therapy,* Moren, et al., Eds, Esevier, Amsterdam, 1985.

The method of the invention includes administering to the pulmonary system an effective amount of a medicament such as, for example, a medicament described above. As used herein, the term "effective amount" means the amount needed to achieve the desired effect or efficacy. The actual effective amounts of drug can vary according to the specific drug or combination thereof being utilized, the particular composition formulated, the mode of administration, and the age, weight, condition of the patient, and severity of the episode being treated. In rescue therapy, the effective amount refers to the amount needed to achieve abatement of symptoms or cessation of the episode. In the case of a dopamine precursor, agonist or combination thereof it is an amount which reduces the Parkinson's symptoms which require rescue therapy. Dosages for a particular patient are described herein and can be determined by one of ordinary skill in the art using conventional considerations, (e.g. by means of an appropriate, conventional pharmacological protocol). For example, effective amounts of L-Dopa range from about 50 to about 500 mg.

Rapid delivery to the medicament's site of action also is preferred. Preferably, the effective amount is delivered on the "first pass" of the blood to the site of action. The "first pass" is the first time the blood carries the drug to and within the target organ from the point at which the drug passes from the lung to the vascular system. Generally, the medicament is released in the blood stream and delivered to its site of action within a time period which is sufficiently short to provide rescue therapy to the patient being treated. In many cases, the medicament can reach the central nervous system in less than about 10 minutes. Preferably, the patient's symptoms abate within minutes and generally no later than one hour. In one embodiment of the invention, the release kinetics of the medicament are substantially similar to the drug's kinetics achieved via the intravenous route. In another embodiment of the invention, the $T_{max}$ of the medicament in the blood stream ranges from about 1 to about 10 minutes. As used herein, the term $T_{max}$ means the point at which levels reach a maximum concentration.

If desired, particles which have fast release kinetics, suitable in rescue therapy, can be combined with particles having sustained release, suitable in treating the chronic aspects of a condition. For example, in the case of Parkinson's disease, particles designed to provide rescue therapy can be co-administered with particles having controlled release properties.

The administration of more than one dopamine precursor, agonist or combination thereof, in particular L-Dopa, carbidopa, apomorphine, and other drugs can be provided, either simultaneously or sequentially in time. These compounds or compositions can be administered before, after or at the same time. Thus, the term "co-administration" is used herein to mean that the specific dopamine precursor, agonist or combination thereof and/or other compositions are administered at times to treat the episodes, as well as the underlying conditions described herein.

The present invention will be further understood by reference to the following non-limiting examples.

Examplifications

EXAMPLE 1

In vivo tests were performed to compare oral and tracheal administration of L-Dopa in an a rat model. Animals received an IP injection of the peripheral decarboxylase inhibitor carbidopa (Sigma, St. Louis, Mo.) (200 mg/kg) one hour prior to administration of L-Dopa. Under ketamine anesthesia, the animals were divided into two groups. In the first group of animals (N=4), L-Dopa (8 mg) was suspended in saline containing 2% methylcellulose and given via oral gavage. In the second group (N=5) a small tracheotomy was performed to permit placement of a pipette tip with a modified 2 mm opening through the trachea and into the lungs. The pipette tip was pre-loaded with powdered L-Dopa (8 mg) and was interfaced with an oxygen tank using silicone tubing. Coinciding with the respiratory cycle of the animal, L-Dopa was pushed into the lungs using a burst of oxygen (5 liters/minute). Blood samples (200 $\mu$l) were withdrawn from a previously placed femoral cannula at the following time points: 0 (immediately prior to L-Dopa administration), 1, 5, 15, 30, 45 and 60 minutes following L-Dopa administration.

Blood levels of L-Dopa, measured, respectively, by mass spectrometry or HPLC, following administration via oral gavage or direct administration into the lungs are shown in FIGS. 1A and 1B. The increase in blood levels of L-Dopa over time following oral administration was modest. In contrast, administration into the lungs produced a robust and rapid rise in L-Dopa levels which peaked between 1 and 5 minutes post drug administration. L-Dopa levels in this group decreased between 5 and 15 minutes and remained stable thereafter. Data are presented as the mean±SEM ng L-Dopa level/ml blood.

Relationship between blood L-Dopa levels and striatal dopamine levels following delivery of L-Dopa either orally or directly into the lungs, as described above, are shown in FIGS. 2A and 2B. FIG. 2A shows blood L-Dopa levels immediately prior to L-Dopa (baseline) and at 2, 15 and 45 minutes following L-Dopa (N=4–6 per time point for each group). Once again, the levels following administration into the lungs show a robust and rapid increase in L-Dopa levels, relative to the modest increases following oral administration.

Figure 2B:
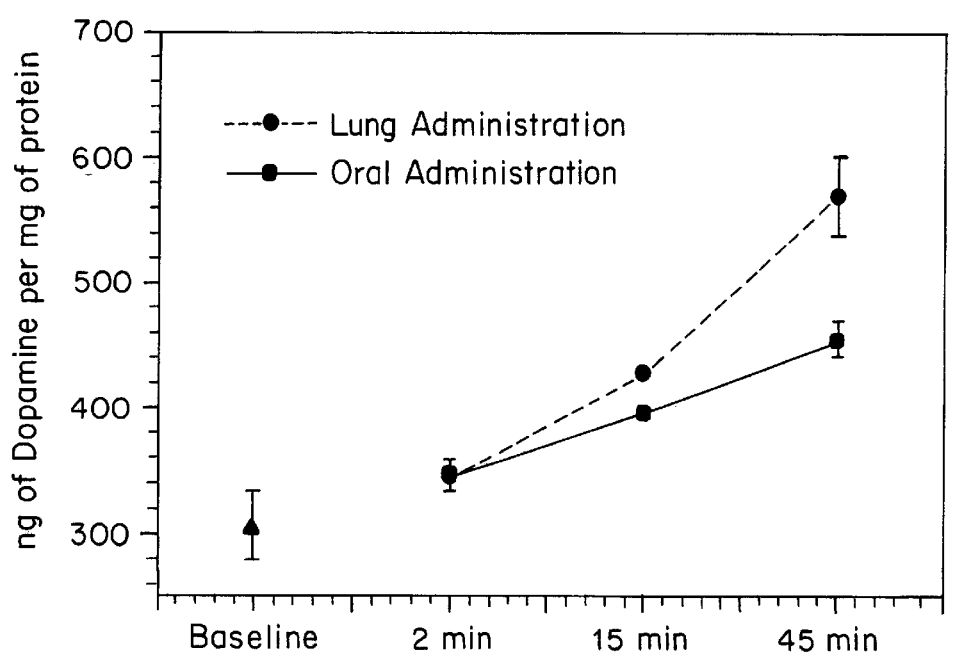
FIG. 2B is a plot representation of striatal dopamine levels in rats following delivery of L-Dopa orally or directly into the lungs.

FIG. 2B shows dopamine levels in the striatum from the same animals shown in FIG. 2A. Immediately following withdrawal of the blood sample, the brains were removed and striatum dissected free. Tissue levels of dopamine were determined using high performance liquid chromatography (HPLC). Note that the marked difference in blood L-Dopa levels seen between the two treatments at two minutes was followed, later in time, by more modest but significant differences in striatal levels of dopamine. Blood levels are presented as the mean±SEM ng L-Dopa levels/ml blood. Striatal levels of dopamine are presented as the mean±SEM ng dopamine/mg protein.

Figure 3:
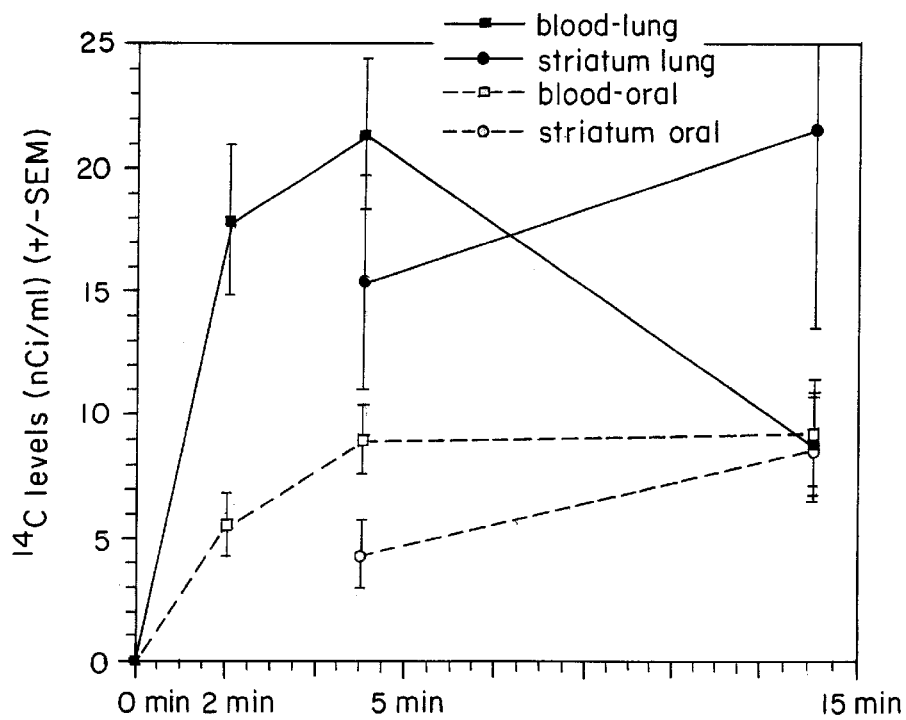
FIG. 3 is a plot representation of blood and striatal levels of $^{14}$C following administration of $^{14}$C-L-Dopa either orally or directly to the lungs.

Blood and striatal levels of $^{14}C$ following administration of $^{14}C$-L-Dopa as generally described above were also determined and are shown in FIG. 3. A total of 25 $\mu$Ci of radiolabeled L-Dopa was mixed with unlabelled L-Dopa to provide a total drug concentration of 8 mg/rat. Blood samples were taken at 2, 5 and 15 minutes post drug administration L-Dopa (N=6 per time point for each group). At 5 or 15 minutes post L-Dopa, the striatum was removed and both the blood and tissues samples were assayed for $^{14}C$ levels using scintillation. The zero minute plasma values are deduced from other many studies using radioactive agents.

Once again, a robust and rapid increase in plasma levels was achieved via the pulmonary route, which was reflected in increased dopamine activity in the brain at both the 5 minute and 15 minute time points (relative to oral administration).

Figure 4:
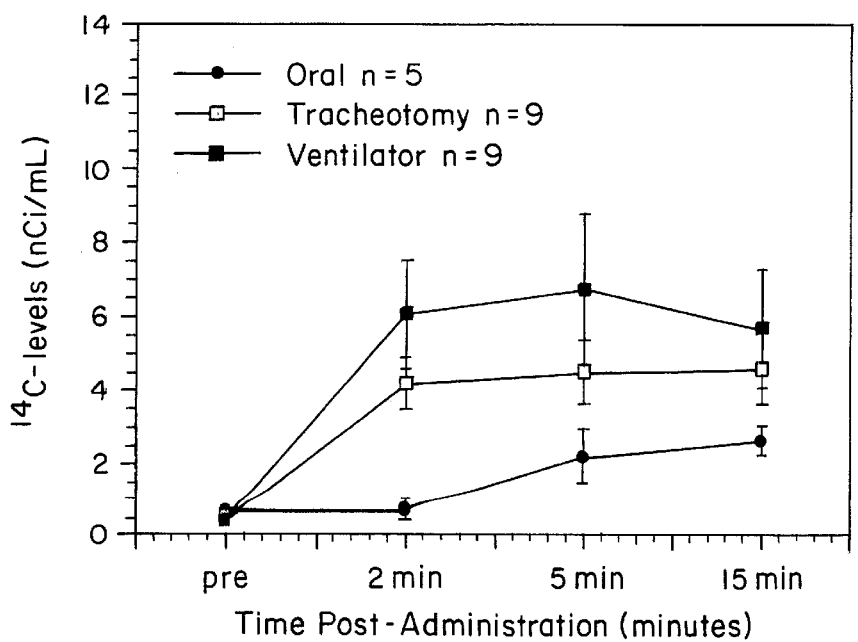
FIG. 4 is a plot representation of plasma $^{14}$C levels in rats following $^{14}$C-L-Dopa administration via gavage, tracheotomy or ventilator.
Figure 5:
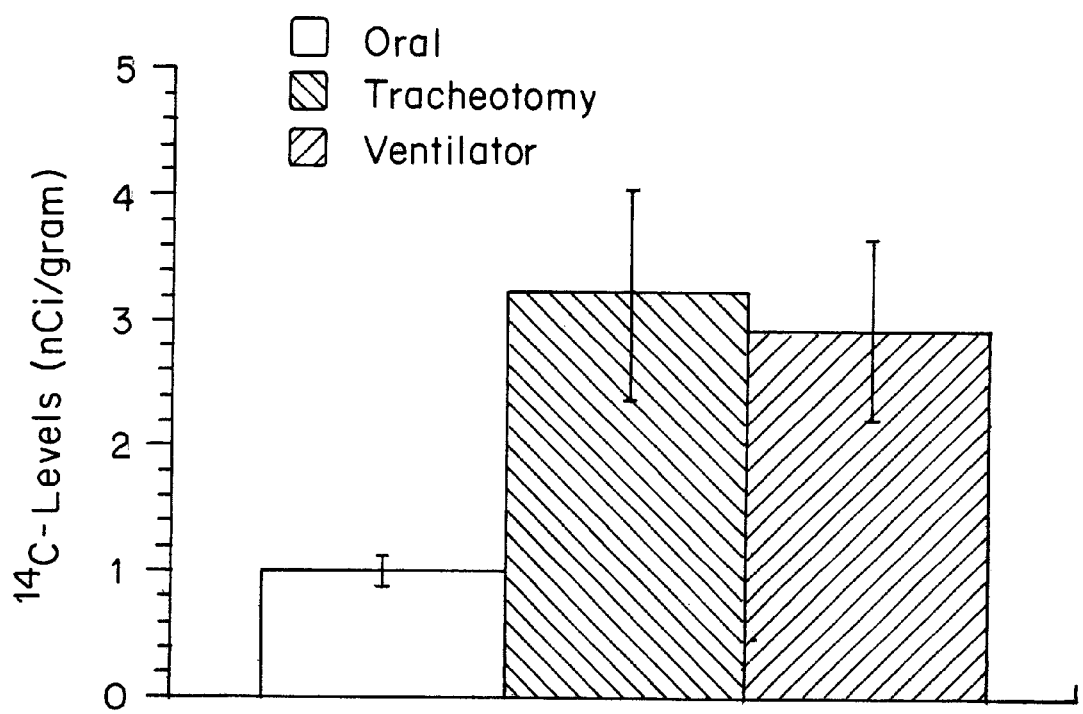
FIG. 5 is a plot representation of brain $^{14}$C levels in rats following $^{14}$C-L-Dopa administration via gavage, tracheotomy or ventilator.
Figure 6A:
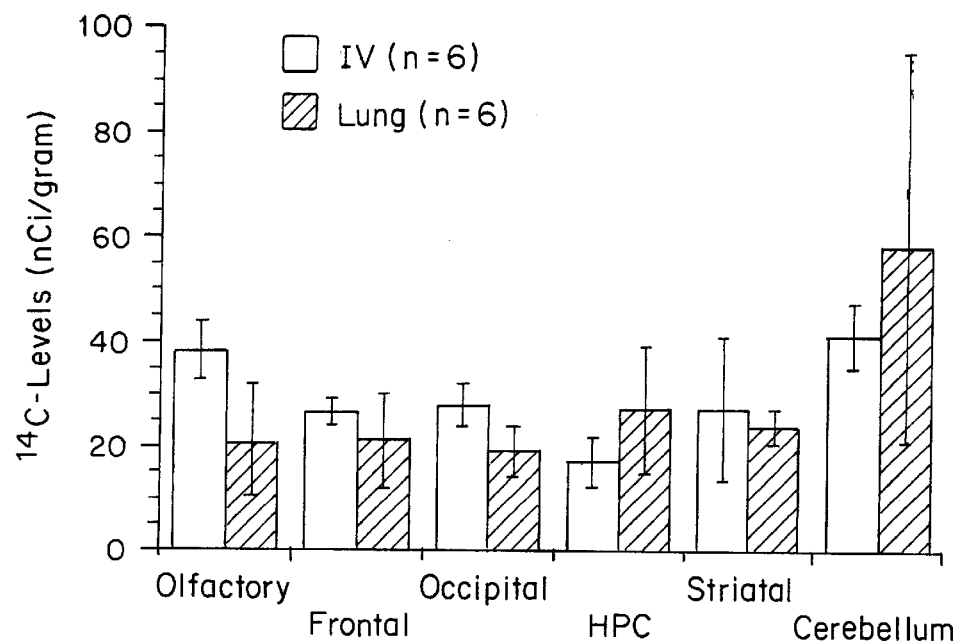
FIG. 6A is a bar graph showing absolute $^{14}$C-Carboplatin levels in regions of the brain following intravenous (IV) and pulmonary administration.
Figure 6B:
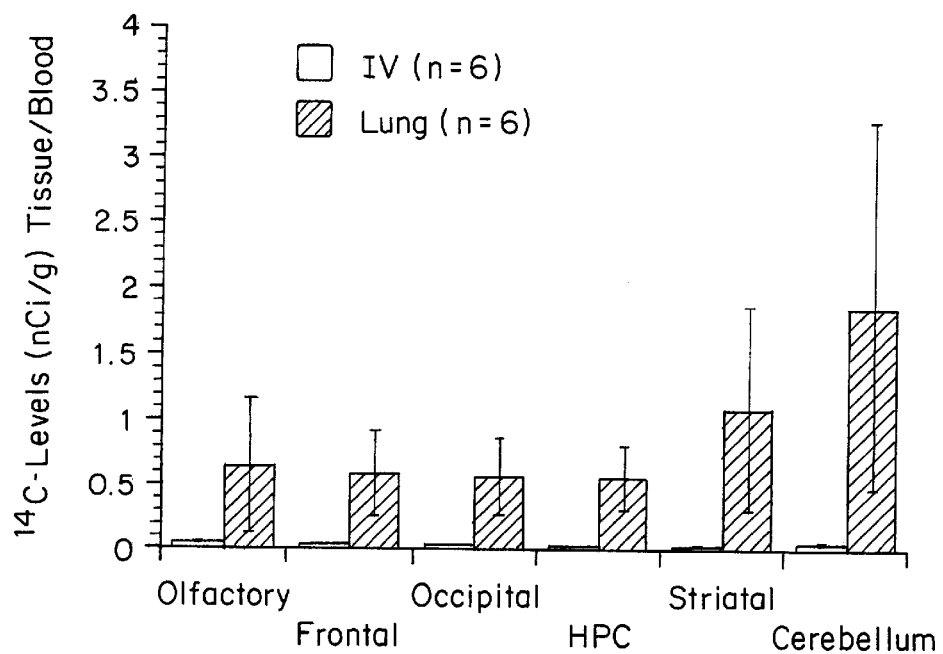
FIG. 6B is a bar graph showing relative $^{14}$C-Carboplatin levels in regions of the brain following intravenous (IV) and pulmonary administration.
Figure 7A:
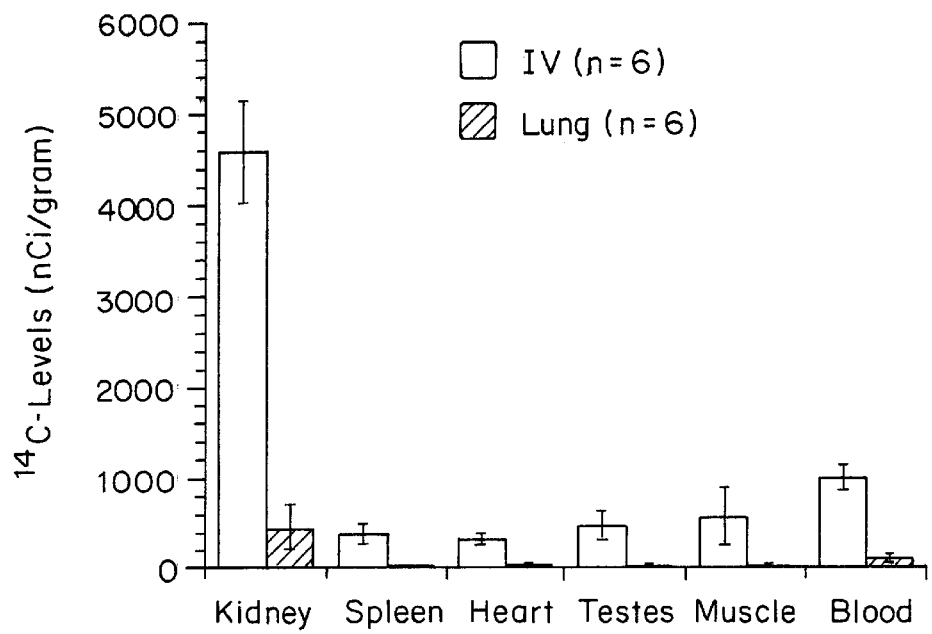
FIG. 7A is a bar graph showing absolute $^{14}$C-Carboplatin levels in animal organs following intravenous (IV) or pulmonary administration.
Figure 7B:
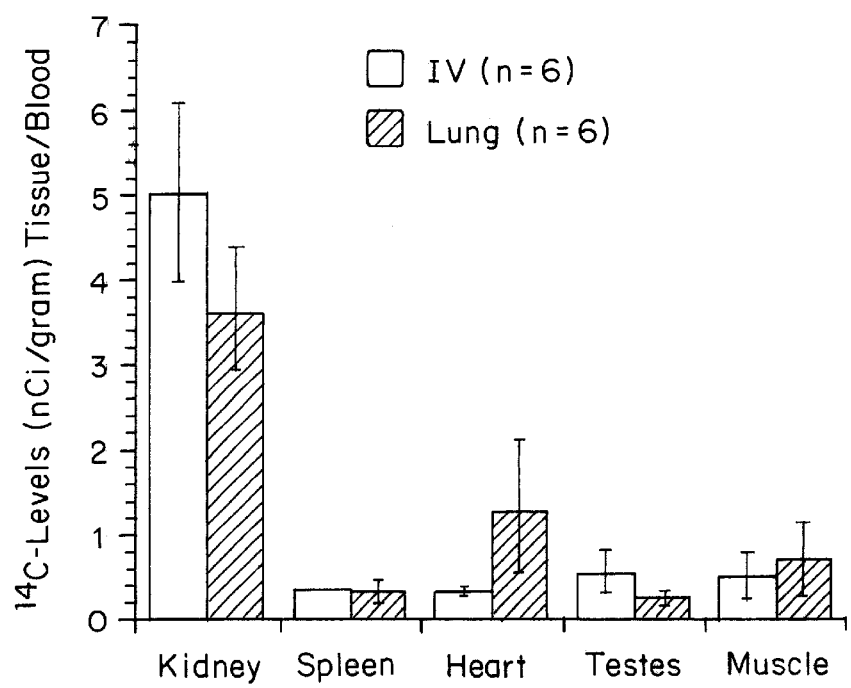
FIG. 7B shows relative $^{14}$C-Carboplatin levels in animal organs following intravenous (IV) or pulmonary administration.
Figure 8:
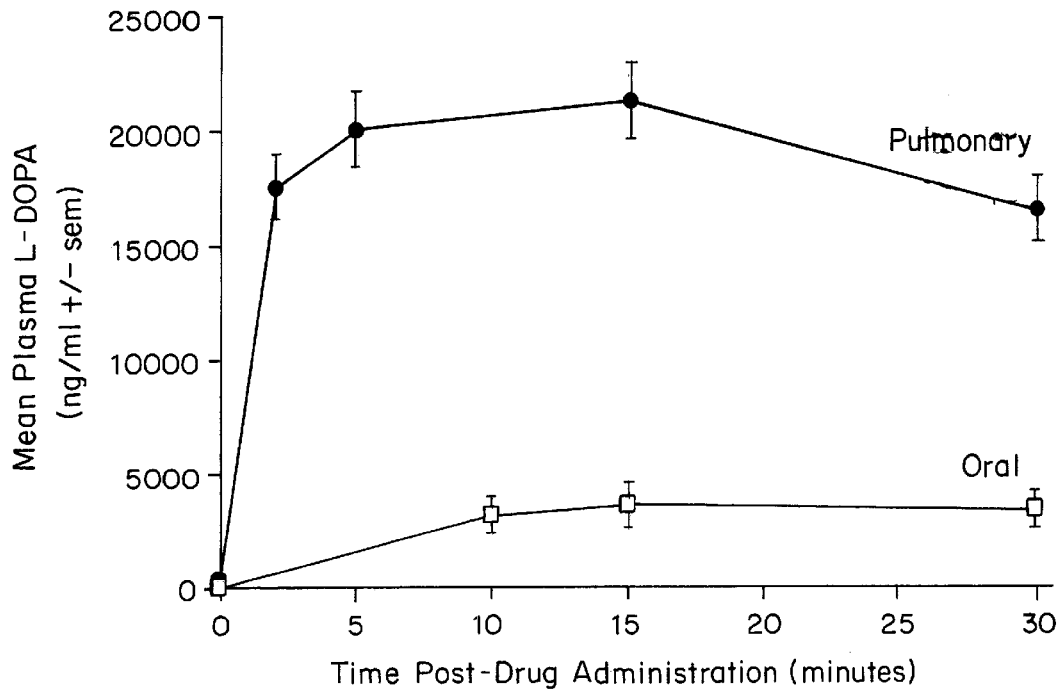
FIG. 8 is a plot representation showing plasma concentration of L-Dopa vs. time following oral or pulmonary administration (normalized for an 8 mg dose).

Direct comparison of plasma $^{14}C$ following administration of $^{14}C$-L-Dopa via oral gavage, inhalation using a tracheotomy (as described above) or ventilator (Harvard Apparatus, Inc., Holliston, Mass.) is shown in FIG. 4. Corresponding brain $^{14}C$-L-Dopa levels are shown in FIG. 5. All animals were briefly anesthetized using 1% Isoflurane and immobilized in a harness to allow blood removal via a previously placed femoral cannula. Blood samples were removed at 0, 2, 5, and 15 minutes post administration. For L-Dopa administration using the ventilator, a 24 gauge catheter was placed within the trachea and the L-Dopa (25 $\mu$Ci) was administered over a 3–5 second period using a tidal volume of 1 ml and 100 strokes/minutes. Striatal tissue samples were processed for determinations of levels of radioactivity using scintillation counts. Both the plasma and brain levels of $^{14}C$ were comparably elevated using both the conventional tracheotomy methods and the ventilator.

EXAMPLE 2

Blood, brain and peripheral organ levels of $^{14}C$ were determined following administration of $^{14}C$-Carboplatin via either IV or pulmonary administration. A total of 100 $\mu$Ci of radiolabeled carboplatin was mixed with unlabelled carboplatin to provide a total drug concentration of 8 mg/rat. All animals were anesthetized using ketamine. For IV administration, carboplatin was administered via a previously placed femoral cannula. For pulmonary administration, a 24 gauge catheter was placed within the trachea and the carboplatin was administered using a Harvard ventilator over a 3–5 second period using a tidal volume of 1 ml and 100 strokes/minutes. Blood samples were taken at 10 minutes post drug administration dopa (N=6 per time point for each group). Brains were removed and dissected into various regions including the olfactory, frontal, and occipital cortices, the hippocampus, striatum, and cerebellum. Peripheral organs included the kidneys, spleen, heart, testes, and muscle. All samples were then processed for determnninations of $^{14}C$ levels using scintillation.

Results are shown in Table 1 and in FIGS. 6A–6B and 7A–7B. Absolute plasma levels of $^{14}C$ were higher following IV administration. However, the absolute brain levels were comparable suggesting that delivery to the brain at this time point was relatively selective. This point is clearer when the ratio of brain to blood $^{14}C$ levels was calculated. Following pulmonary delivery, $^{14}C$ levels were 2833% higher than observed following IV administration. Absolute levels of $^{14}C$ in peripheral tissue was also lower following pulmonary administration (92% lower relative to IV). In contrast to the large differences in selectivity seen in the brain, the relative peripheral selectivity (derived from dividing the levels of radioactivity in peripheral organs by that in the blood) was only 47% higher in the pulmonary group. Interestingly though, the highest levels of $^{14}C$ in peripheral tissue were found in the heart. Together, these data suggest that the brain and the heart may represent sites of preferential delivery at time point immediately following pulmonary drug administration.

TABLE 1

Scintillation Counts of $^{14}C$-Levels in Plasma, Brain and Peripheral Organs Following $^{14}C$-Carboplatin (100 $\mu$Ci/8 mg) Administration

|  |  | 10 Minutes |
|---|---|---|
| Plasma Levels | IV | 994.348 |
|  | Lung | (n = 6) |
|  | (% Difference) | 102.215 |
|  |  | −89.72% |
|  |  | (n = 6) |
| Absolute Brain | IV | 29.47 |
| Levels | Lung | 27.29 |
| (nCi/gram) |  |  |
| Relative Brain | IV | 0.03 |
| Selectivity | Lung | 0.88 |
| (Brain/Blood) | (% Difference) | +2833% |
| (Brain/Blood) | IV(Br/Bl)/Lung(Br/Bl) |  |
| (Brain/Blood) |  |  |
| Absolute Tissue | IV | 0.03 |
| Levels | Lung | 0.88 |
| (Peripheral Organs) | (% Difference) | +2833% |
| *excludes kidney | IV(Br/Bl)/Lung(Br/Bl) |  |
| Relative | IV | 0.44 |
| Peripheral | Lung | 0.65 |
| Selectivity | (% Difference) | +47.727% |
| (Peripheral/Blood) | IV(Per/Bl)/Lung(Per/Bl) |  |
| *excludes kidney |  |  |

EXAMPLE 3

Particles comprising L-Dopa and suitable for inhalation were produced as follows. 2.00123 g DPPC (Avanti Polar Lipids, Lot #G160PC-25) was added to 2.80 L of ethanol and stirred to dissolve. 0.0817 g L-Dopa (Spectrum, Lot 0Q0128, Laguna Hills, Calif.), 0.9135 g Sodium Citrate (Dehydrate) (Spectrum Lot NX0195), and 0.5283 g Calcium Chloride (Dehydrate) (Spectrum Lot NT0183) were added to 1.2 L of water and dissolved. The solutions were combined by adding the water solution to the ethanol solution and then the solutions were allowed to stir until the solution was clear. The weight percent of the formulation was approximately: 20% L-Dopa, 50% DPPC, 20% Sodium Citrate, 10% Calcium Chloride.

The final solution was then spray dried in a Niro dryer (Niro, Inc., Columbus, Md.) using a rotary atomizer and nitrogen drying gas following the direction of the manufacturer, using the following spray conditions: $T_{inlet}$=120 C, $T_{outlet}$=54 C, Feed Rate=65 ml/min, Heat Nitrogen=38 mm H20, Atomizer Speed=20,000 rpm (V24 atomizer used).

The resulting particle characteristics were: Mass Median Aerodynamic Diameter (MMAD)=2.141 μm and Volume Median Geometric Diameter (VMGD)=10.51 μm.

Under etamine anesthesia, six rats received pulmonary administration of the formulation described above (20/50/20/10 L-Dopa/DPPC/Sodium Citrate/Calcium Chloride).

The results are shown in FIG. 8. This figure shows blood levels of L-Dopa following administration via oral gavage or direct administration into the lungs via insufflation. L-Dopa levels were measured using both HPLC. Animals received an IP injection of the peripheral decarboxylase inhibitor carbi-dopa (200 mg/kg) 1 hour prior to administration of L-Dopa. Under ketamine anesthesia, the animals were divided into 2 groups. In the first group, animals were fasted overnight and L-Dopa (8 mg) was suspended in saline contained 1% methylcellulose and given via oral gavage. In the second group, insufflation was used to delivery the L-Dopa formulation directly into the lungs. Blood samples (200 μl) were withdrawn from a previously placed femoral cannula at the following time points: 0 (immediately prior to L-Dopa administration), 2, 5, 15, and 30 minutes following L-Dopa administration. The increase in blood levels of L-Dopa over time following oral administration was modest. In contrast, administration into the lungs produced a robust and rapid rise in L-Dopa levels. L-Dopa levels in this group remained elevated relative to oral delivery at 30 minutes post drug administration. Data were normalized to a dose of 8 mg/kg (the total oral gavage dose). Data are presented as the mean±SEM ng 1-Dopa levels/ml blood.

EXAMPLE 4

Ketoprofen/DPPC/maltodextrin particles were prepared and administered in vivo.

Ketoprofen (99.5%) was obtained from Sigma, (St. Louis, Mo.), dipalmitoyl phosphatidyl choline (DPPC) from Avanti Polar Lipids, (Alabaster, Ala.) and maltodextrin,M100 (Grain Processing Corp., Muscatine, Iowa).

To prepare ketoprofin/DPPC/Maltodextrin solutions, maltodextrin (0.598 g) was added to 0.60 L USP water. DPPC (0.901 g) was added to 1.40 L ethanol and stirred until dissolved. The water and ethanol solutions were combined, resulting in a cloudy solution. 500 ml of this stock solution was used for each run. The addition of ketoprofen to the DPPC/Maltodextrin stock solution is described in Table 2.

A Niro Atomizer Portable Spray Dryer (Niro, Inc., Columbus, Md.) was used to produce the dry powders. Compressed air with variable pressure (1 to 5 bar) ran a rotary atomizer (2,000 to 30,000 rpm) located above the dryer. Liquid feed of the ketoprofin/DPPC/Maltodextrin solutions, with varying rate (20 to 66 ml/min), was pumped continuously by an electronic metering pump (LMI, model #A151-192s) to the atomizer. Both the inlet and outlet temperatures were measured. The inlet temperature was controlled manually; it could be varied between 100° C. and 400° C., with a limit of control of 5° C. The outlet temperature was determined by the inlet temperature and such factors as the gas and liquid feed rates: it varied between 50° C. And 130° C. A container was tightly attached to the 6" cyclone for collecting the powder product. The spraying conditions for each solution is given in Table 3, which shows that the spraying conditions were held nearly constant throughout the study. The total recovery and yield for each solution is given in Table 4.

The particles were characterized using the Aerosizer (TSI, Inc., Amherst, Mass.) and the RODOS dry powder dispenser (Sympatec Inc., Princeton, N.J.) as instructed by the manufacturer. For the RODOS, the geometric diameter was measured at 2 bars. The material from run #5 was also characterized using a gravimetric collapsed Andersen Cascade Impactor (ACI, 2 stage, Anderson Inst., Sunyra, Ga.). The samples were examined using a scanning electron microscope (SEM).

Table 4 indicates that increasing the weight % of ketoprofen led to a decrease in yield. The addition of ketoprofen to the stock solution linearly decreased yield. This may be due to a decrease in melting temperature for DPPC when mixed with ketoprofen, leading to the yield loss.

Table 5 shows that the particles ranged in diameter from 8.8 to 10.2 mm (VMGD) and from 2.65 to 3.11 (MMAD). The lowest MMAD particles were for the 8.4% loading material (run #5).

Table 6 shows the results of a Andersen Collapsed Impactor study (ACI, gravimetric, n=2) of the material from run #5, the 8.4% loading material. The FPF below 5.6 μm and below 3.4 μm are consistent with respirable powders which are reasonably respirable.

TABLE 2

| Sample ID | Ketoprofen added (mg) | Total solids (g/L) | % Ketoprofen |
|---|---|---|---|
| Run #1 | 0 | 1.000 | 0 |
| Run #2 | 8.0 | 1.016 | 1.6 |
| Run #3 | 15.1 | 1.030 | 3.0 |
| Run #4 | 30.1 | 1.060 | 5.7 |
| Run #5 | 46.0 | 1.092 | 8.4 |
| Run #6 | 63.0 | 1.126 | 11.2 |

TABLE 3

| Sample | Temperature (° C.) | | Liquid Feed | Gas Pressure | Rotor Speed | Inlet Dew-point |
|---|---|---|---|---|---|---|
| ID | Inlet | Outlet | (ml/min) | (mm $H_2O$) | (RPM) | (° C.) |
| Run #1 | 115 | 36 | 75 | 40 | 18,600 | −27.0 |
| Run #2 | 113 | 38 | 85 | 40 | 18,400 | −26.8 |
| Run #3 | 110 | 38 | 85 | 39 | 18,300 | −26.4 |
| Run #4 | 110 | 39 | 85 | 38 | 18,400 | −25.9 |
| Run #5 | 110 | 38 | 86 | 39 | 18,400 | −25.4 |
| Run #6 | 110 | 38 | 85 | 38 | 18,400 | −25.0 |

TABLE 4

| Sample ID | Weight Collected (mg) | Theoretical Yield (mg) | Actual Yield (% Theoretical) |
|---|---|---|---|
| Run #1 | 86 | 500 | 37.2 |
| Run #2 | 195 | 508 | 38.4 |
| Run #3 | 47 | 515 | 28.5 |
| Run #4 | 127 | 530 | 24.0 |

TABLE 4-continued

| Sample ID | Weight Collected (mg) | Theoretical Yield (mg) | Actual Yield (% Theoretical) |
|---|---|---|---|
| Run #5 | 89 | 546 | 16.3 |
| Run #6 | 67 | 563 | 11.9 |

TABLE 5

| Sample ID | MMAD ($\mu$m) | Std Dev | MGVD ($\mu$m, 2 bar) |
|---|---|---|---|
| Run #1 | 3.11 | 1.48 | 9.0 |
| Run #2 | 3.01 | 1.37 | 9.3 |
| Run #3 | 2.83 | 1.40 | 10.3 |
| Run #4 | 2.84 | 1.41 | 10.4 |
| Run #5 | 2.65 | 1.39 | 9.8 |
| Run #6 | 2.83 | 1.38 | 8.8 |

TABLE 6

| | |
|---|---|
| Stage 0 | 1.33 mg |
| Stage 2 | 2.75 mg |
| Stage F | 3.17 mg |
| Capsule Fill | 12.37 mg |
| Weight < 5.6 $\mu$m | 5.92 |
| FPF$_{5.6}$ | 0.479 |
| Weight < 3.4 $\mu$m | 3.17 |
| FPF$_{3.4}$ | 0.256 |

350 mg of 8% ketoprofen in 60/40 DPPC/maltodextrin were produced as described above and administered to 20 sprague Dawley rats. Each of 8 rats were given 7 mg of powder via insufflation, and each of 7 rats were given 7 mg of powder dissolved in 50% ethanol orally. Time points were set at 0, 5, 15, 30, 60, 120, 240, 360 and 480 minutes. For t=0, 4 animals were tested without dosing. For each time point after, samples were taken from either 3 or 4 rats. Each rat was used for 4 time points, with 3 or 4 animals each in four groups. The animals were distributed as follows: 3 animals oral 5, 30, 120, 360; 4 animals insufflation 15, 60, 240, 480. Sufficient blood was drawn at each time point for the ketoprofen plasma assay. Blood samples were centrifuged, the plasma collected and then frozen at −20° C. prior to shipment to the contract laboratory for analysis. The assay used in this study has a lower detection limit of 1.0 mg/ml.

Rats were dosed with ketoprofen via either oral or pulmonary administration to determine if the pulmonary route would alter the time required to achieve maximum plasma concentration. The results show that the pulmonary delivery route leads to a very rapid uptake with $C_{max}$ occurring at $\leq$10 minutes. The rats that received oral doses of ketoprofen displayed somewhat anomalous pharmacokinetic behavior, with the relative bioavailability being about half of that displayed for rats dosed via the pulmonary route. This result was unexpected as ketoprofen is 90% orally bioavailable in the human model. This anomaly for the orally dosed rats does not, however, invalidate the significance of the early $C_{max}$ seen for the rats dosed via the pulmonary route.

Figure 9:
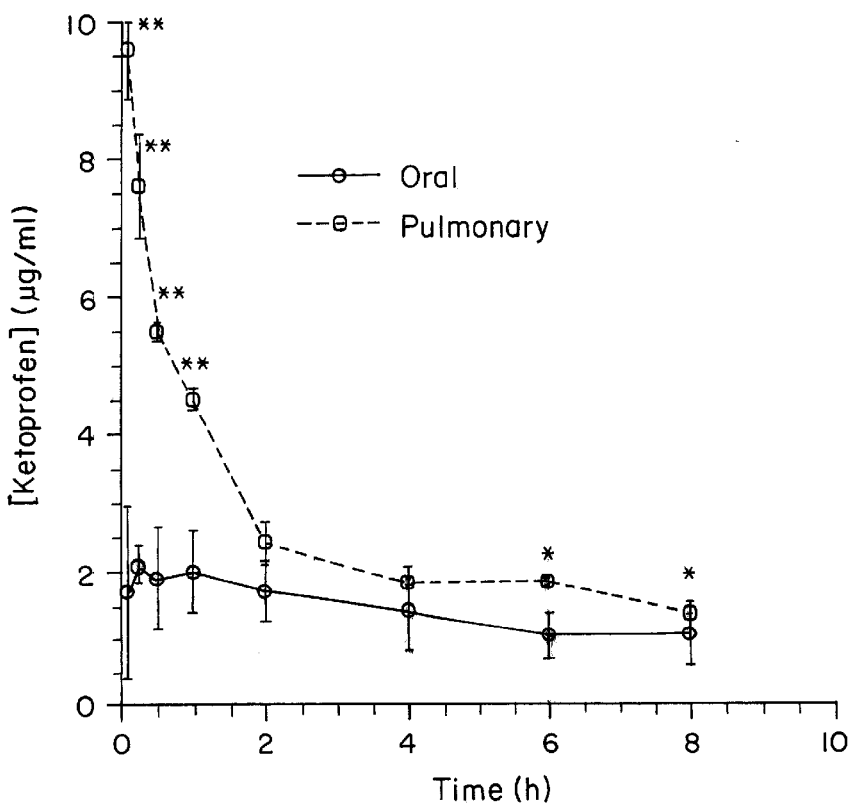
FIG. 9 is a plot representation showing plasma concentration of ketoprofen vs. time for oral and pulmonary groups.
Figure 10:
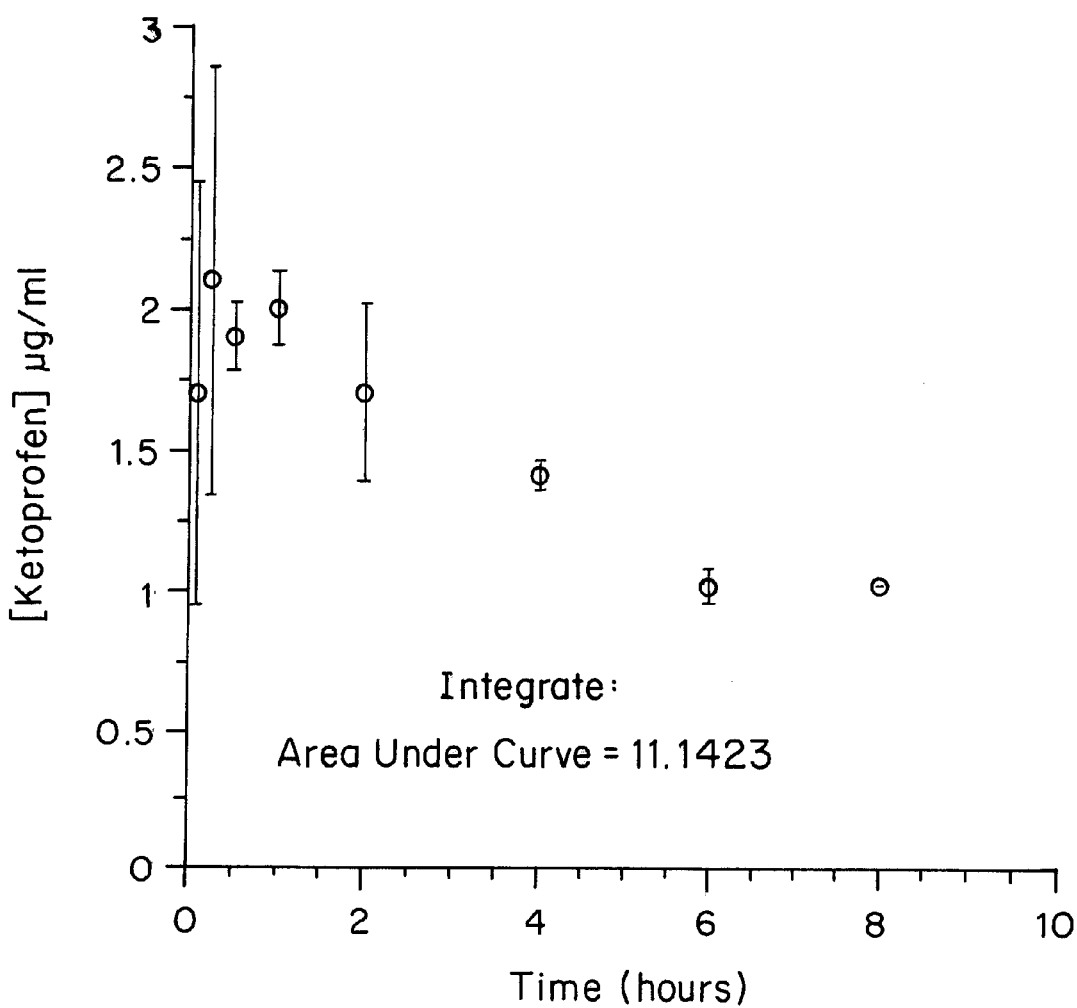
FIG. 10 is a plot representation showing plasma concentration of ketoprofen vs. time for oral group
Figure 11:
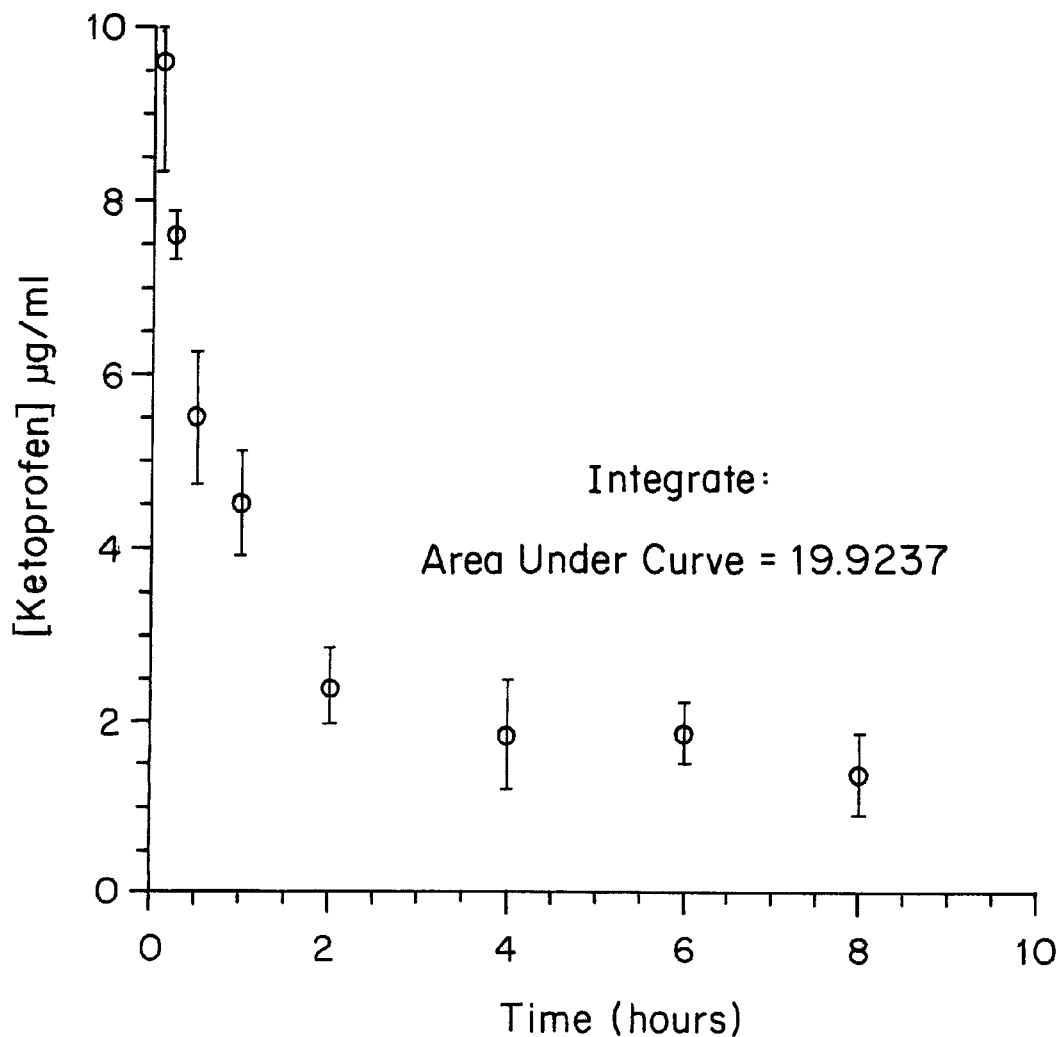
FIG. 11 is a plasma concentration of ketoprofen vs. time for pulmonary group.

The results are provided in Table 7. The averages were calculated along with the standard errors and p values. The results are also presented graphically in FIGS. 9–11, wherein FIG. 9 shows both data sets, FIG. 10 gives the oral dosing results and FIG. 11 shows the insufflation results. For FIG. 9, points with p<0.05 are marked with "*" and points with p<0.01 are marked with "**". For FIGS. 10 and 11, AUC (area under the curve) was performed via numerical integration of the curve with smooth interpolation.

At t=0, all rats showed ketoprofen levels below the detection limit for the assay. From t=5 min to t=60 min, the insulflated rats had significantly higher plasma levels of ketoprofen. At t=120 min and t=240 min, the plasma levels of ketoprofen of the two groups were statistically equivalent. At t=360 min and t=480, the plasma levels of ketoprofen for both groups approached the detection limit for the assay.

The ratio of the AUCs for insulflated rats vs. orally dosed was about 2. Since the plasma concentrations for ketoprofen at the early time points were statistically significant as well. $C_{max}$ for the insulflated rats clearly occurred <15 min and $C_{max}$ for the orally dosed rats occurred between 15–60 min. Due to the large standard error and the relatively low plasma levels for this group, it is not possible to accurately determine the time required for $C_{max}$.

Pulmonary administration resulted in $C_{max}$ occurring very quickly (<15 min) compared to oral dosing (t=15 to 60 min).

The insulflated rats showed higher bioavailability compared to the orally dosed rats. This is unexpected as previous studies have shown ketoprofen to have consistently high (>90%) bioavailability in humans when dosed orally, subcutaneously or rectally. Since the pharmokinetic behavior of ketoprofen delivered orally is well-known, the anomalous results seen here for the orally dosed group do not invalidate the results seen for the insufflation group.

TABLE 7

| Time Min. | Oral Dosing Avg. (ug/ml) | Group St. Dev. | Pulmonary Avg. (ug/ml) | Dosing Group Std. Dev. | P Value |
|---|---|---|---|---|---|
| 0 | 1.0 | N/A | 1.0 | N/A | |
| 5 | 1.7 | 0.75 | 9.6 | 1.27 | 0.0003 |
| 15 | 2.1 | 0.76 | 7.6 | 0.28 | 0.0000 |
| 30 | 1.9 | 0.12 | 5.5 | 0.76 | 0.0012 |
| 60 | 2.0 | 0.13 | 4.5 | 0.60 | 0.0002 |
| 120 | 1.7 | 0.31 | 2.4 | 0.44 | 0.0929 |
| 240 | 1.4 | 0.05 | 1.8 | 0.63 | 0.2554 |
| 360 | 1.0 | 0.06 | 1.8 | 0.35 | 0.0224 |
| 480 | 1.0 | 0.00 | 1.3 | 0.47 | 0.2174 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of providing rescue therapy in the treatment of Parkinson's disease comprising:
   administering to the respiratory tract of a patient in need of rescue therapy particles comprising an effective amount of a dopamine precursor, a dopamine agonist or any combination thereof,
   wherein the particles are delivered to the pulmonary system and the dopamine precursor, the dopamine agonist or the combination thereof is released in the blood stream of the patient and reaches the central nervous system to provide said rescue therapy.

2. The method of claim 1 wherein the particles comprise levodopa.

3. The method of claim 2 wherein the levodopa is present in the particles in an amount ranging from about 1 to about 90 weight percent.

4. The method of claim 2 wherein the particles further comprise carbidopa.

5. The method of claim 1 wherein the particles comprise apomorphine.

6. The method of claim 1 wherein the particles further comprise a material selected from the group consisting of a phospholipid or combination of phospholipids, an amino acid, a hydroxydicarboxylic acid, a hydroxytricarboxylic acid, a salt of any of said acids, a multivalent metal salt and any combination thereof.

7. The method of claim 6 wherein the particles comprise a phospholipid or combination of phospholipids.

8. The method of claim 7 wherein the phospholipid or combination of phospholipids is present in the particles in an amount ranging from about 10 weight percent to about 99 weight percent.

9. The method of claim 1 wherein the particles have a matrix transition temperature that is no higher than the patient's physiological temperature.

10. The method of claim 6 wherein the particles comprise a hydroxydicarboxylic acid, a hydroxytricarboxylic acid or a salt of any of said acids.

11. The method of claim 10 wherein the particles comprise citrate.

12. The method of claim 10 wherein the particles further comprise a multivalent metal salt.

13. The method of claim 12 wherein the multivalent metal salt is calcium chloride.

14. The method of claim 9 wherein the material is present in the particles in an amount of at least 10 weight percent.

15. The method of claim 1 wherein the particles have a tap density less than about 0.4 g/cm$^3$.

16. The method of claim 15 the particles have a tap density less than about 0.1 g/cm$^3$.

17. The method of claim 1 wherein the particles have a volume median geometric diameter of between about 5 micrometers and about 30 micrometers.

18. The method of claim 1 wherein the particles have an aerodynamic diameter of between about 1 and about 5 microns.

19. The method of claim 18 wherein the particles have an aerodynamic diameter of between about 1 and about 3 microns.

20. The method of claim 1 wherein delivery to the pulmonary system is by means of a dry powder inhaler.

21. The method of claim 1 wherein delivery to the pulmonary system is by means of a metered dose inhaler.

22. The method of claim 1 wherein the patient is suffering with late stage Parkinson's disease.

23. Particles suitable for delivery to the pulmonary system comprising a dopamine precursor, a dopamine agonist or any combination thereof and a material selected from the group consisting of a phospholipid or combination of phospholipids, an amino acid, a hydroxydicarboxylic acid, a hydroxytricarboxylic acid, a salt of any of said acids, a multivalent metal salt and any combination thereof.

24. The particles of claim 23 wherein the particles comprise levodopa.

25. The particles of claim 24 wherein the levodopa is present in the particles in an amount ranging from about 1 to about 90 weight percent.

26. The particles of claim 24 wherein the particles further comprise carbidopa.

27. The particles of claim 23 wherein the particles comprise apomorphine.

28. The particles of claim 23 wherein the particles comprise a phospholipid or combination of phospholipids.

29. The particles of claim 28 wherein the phospholipid or combination of phospholipids is present in the particles in an amount ranging from about 10 weight percent to about 99 weight percent.

30. The particles of claim 28 wherein the particles have a matrix transition temperature that is no higher than the patient's physiological temperature.

31. The particles of claim 23 wherein the particles comprise a hydroxydicarboxylic acid, a hydroxytricarboxylic acid, or any salt of said acids.

32. The particles of claim 31 wherein the particles comprise citrate.

33. The particles of claim 31 wherein the particles further comprise a multivalent metal salt.

34. The particles of claim 33 wherein the multivalent metal salt is calcium chloride.

35. The particles of claim 23 wherein the material is present in the particles in an amount of at least 10 weight percent.

36. The particles of claim 23 wherein the particles have a tap density less than about 0.4 g/cm$^3$.

37. The particles of claim 36 wherein the particles have a tap density less than about 0.1 g/cm$^3$.

38. The particles of claim 23 wherein the particles have a volume median geometric diameter of between about 5 micrometers and about 30 micrometers.

39. The particles of claim 23 wherein the particles have an aerodynamic diameter of between about 1 and about 5 microns.

40. The particles of claim 39 wherein the particles have an aerodynamic diameter of between about 1 and about 3 microns.

41. Particles suitable for delivery to the pulmonary system comprising:

a dopamine precursor, a dopamine agonist or any combination thereof;

a phospholipid or combination of phospholipids; and a material selected from the group consisting of an amino acid, a hydroxydicarboxylic acid, a hydroxytricarboxylic acid, a salt of any of said acids, a multivalent metal salt and any combination thereof.

42. Particles suitable for delivery to the pulmonary system comprising:

a dopamine precursor, a dopamine agonist or any combination thereof;

a saccharide; and a material selected from the group consisting of a phospholipid or combination of phospholipids, an amino acid, a hydroxydicarboxylic acid, a hydroxytricarboxylic acid, a salt of any of said acids, a multivalent metal salt and any combination thereof.

* * * * *

UNITED STATES PATENT AND TRADEMARK OFFICE
CERTIFICATE OF CORRECTION

PATENT NO.    : 6,514,482 B1
DATED         : February 4, 2003
INVENTOR(S)   : Raymond T. Bartus and Dwaine F. Emerich It is certified that error appears in the above-identified patent and that said Letters Patent is hereby corrected as shown below:

<u>Column 23,</u>
Line 13, delete "1" and insert -- 7 --;
Line 29, after "15" insert -- wherein --.

Signed and Sealed this

Tenth Day of June, 2003

JAMES E. ROGAN
*Director of the United States Patent and Trademark Office*